US010307273B2

(12) United States Patent
Rubesch et al.

(10) Patent No.: US 10,307,273 B2
(45) Date of Patent: Jun. 4, 2019

(54) STENT WITH ANTI-MIGRATION FEATURES

(71) Applicant: BOSTON SCIENTIFIC SCIMED, INC., Maple Grove, MN (US)

(72) Inventors: Timothy L. Rubesch, Blaine, MN (US); John A. Hingston, Framingham, MA (US); Michael D. Amos, Ayer, MA (US); Terry V. Brown, Fridley, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 147 days.

(21) Appl. No.: 15/055,510

(22) Filed: Feb. 26, 2016

(65) Prior Publication Data

US 2016/0256296 A1    Sep. 8, 2016

Related U.S. Application Data

(60) Provisional application No. 62/127,486, filed on Mar. 3, 2015.

(51) Int. Cl.
*A61F 2/24* (2006.01)
*A61F 2/848* (2013.01)
*A61F 2/90* (2013.01)
*A61F 2/07* (2013.01)
*A61F 2/04* (2013.01)

(52) U.S. Cl.
CPC ............... *A61F 2/848* (2013.01); *A61F 2/90* (2013.01); *A61F 2002/041* (2013.01); *A61F 2002/047* (2013.01); *A61F 2002/048* (2013.01); *A61F 2002/072* (2013.01); *A61F 2002/8483* (2013.01); *A61F 2210/0076* (2013.01)

(58) Field of Classification Search
CPC .. A61F 2/2418; A61F 2220/0016; A61F 2/07; A61F 2250/0069; A61F 2/86; A61F 2/848
See application file for complete search history.

(56) References Cited

U.S. PATENT DOCUMENTS

| 5,405,377 A | 4/1995 | Cragg |
| 5,527,354 A | 6/1996 | Fontaine et al. |
| 5,792,400 A | 8/1998 | Talja et al. |
| 5,993,482 A | 11/1999 | Chuter |
| 6,613,076 B1 | 9/2003 | Cherif-Cheikh |
| 7,070,617 B2 | 7/2006 | Kula et al. |

(Continued)

FOREIGN PATENT DOCUMENTS

| EP | 0799607 A2 | 10/1997 |
| EP | 0806190 A1 | 11/1997 |
| WO | 2014030982 A1 | 2/2014 |

*Primary Examiner* — Ann Schillinger
(74) *Attorney, Agent, or Firm* — Seager, Tufte & Wickhem, LLP

(57) ABSTRACT

An implantable medical device for implantation within a passageway of a patient comprises a stent including a plurality of wires, at least one of the plurality of wires having a cross-section having a first tapered point, and a covering layer having an inner diameter and an outer diameter. In some embodiments, the plurality of wires may be disposed at least partially around the covering layer. Additionally in some embodiments, the first tapered point may extend outward further than the outer diameter of the covering layer.

20 Claims, 28 Drawing Sheets

(56) References Cited

U.S. PATENT DOCUMENTS

| | | |
|---|---|---|
| 7,959,671 B2 | 6/2011 | Mangiardi et al. |
| 8,311,633 B2 | 11/2012 | Ransbury et al. |
| 9,161,836 B2 * | 10/2015 | Rolando ............... A61F 2/2409 |
| 9,861,467 B2 * | 1/2018 | Cully ................. A61B 17/0057 |
| 2011/0112626 A1 | 5/2011 | van der Leest |
| 2014/0121756 A1 | 5/2014 | Perko |

* cited by examiner

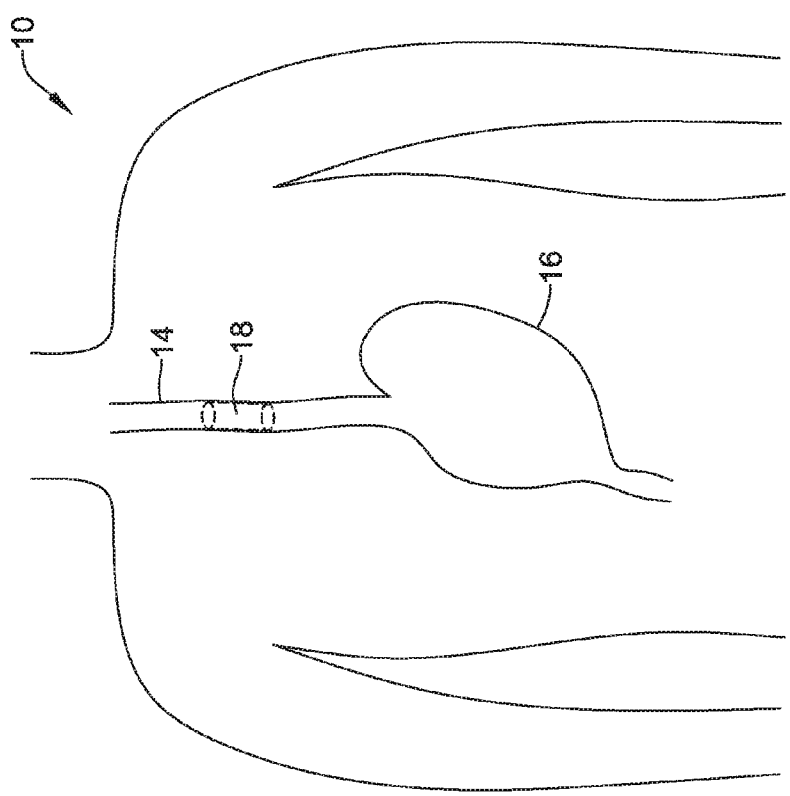

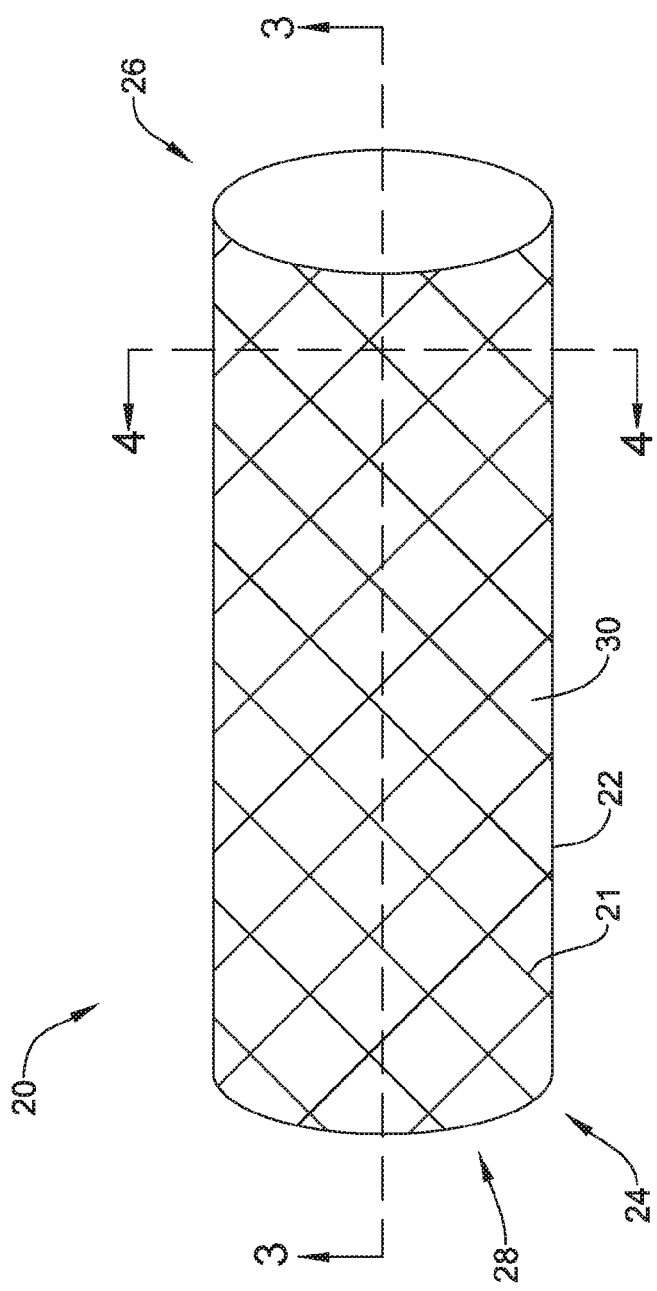

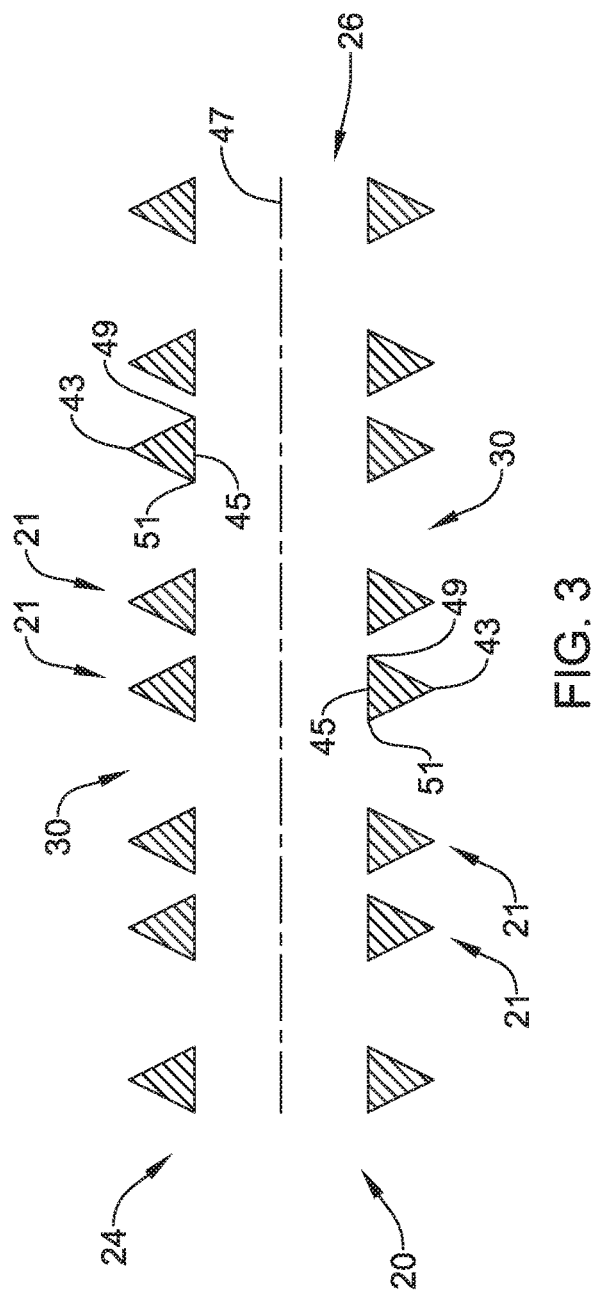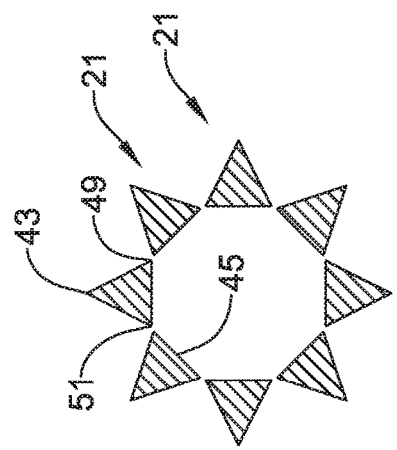

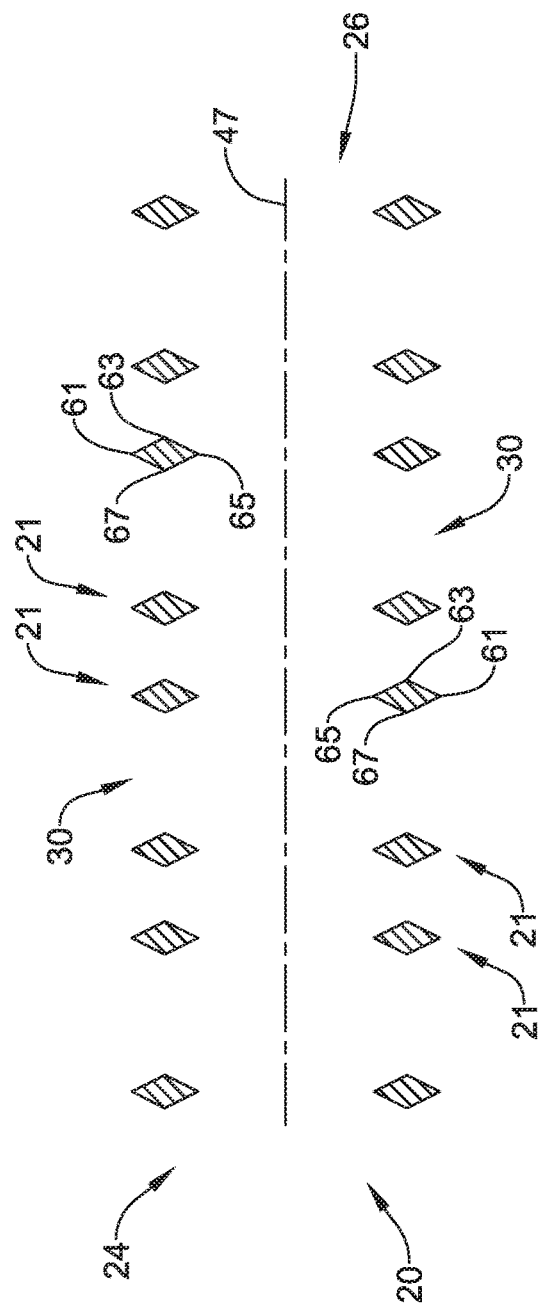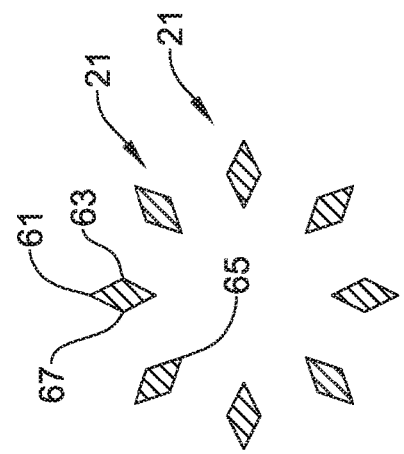

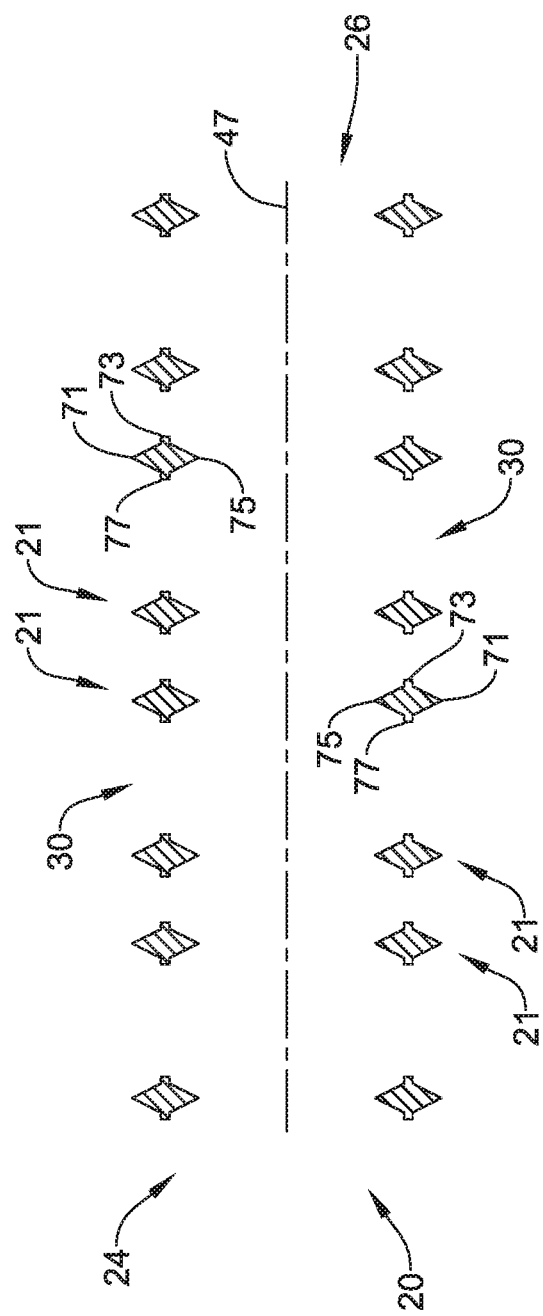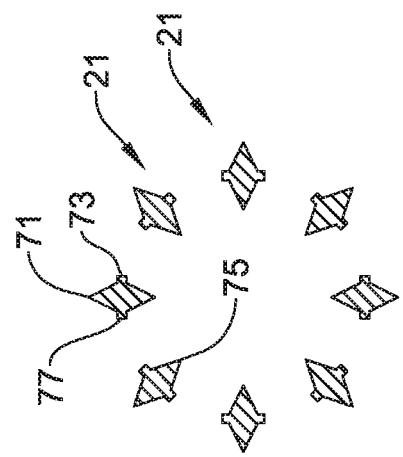

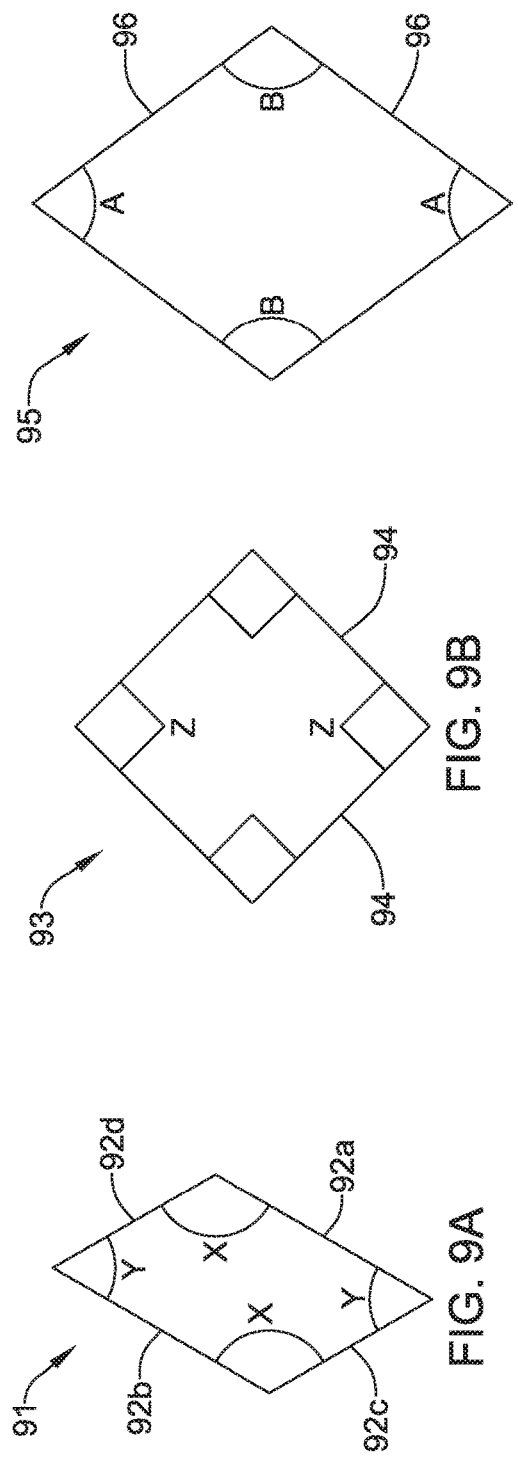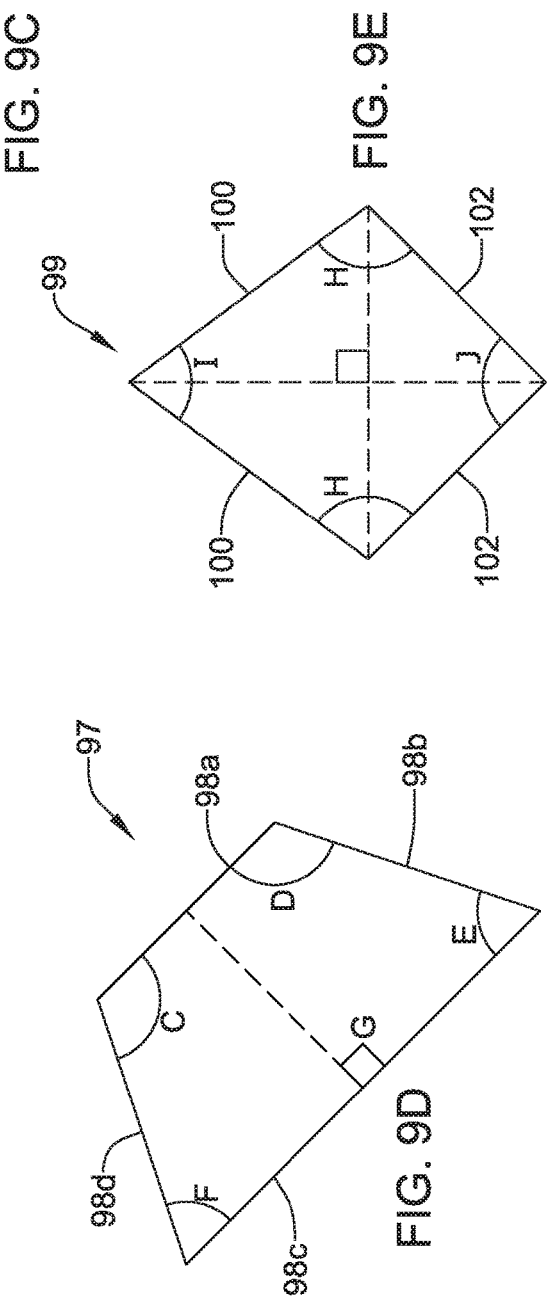

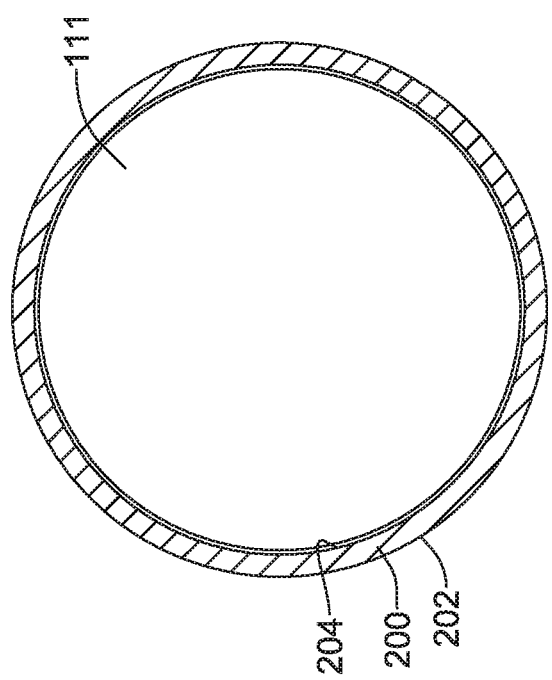

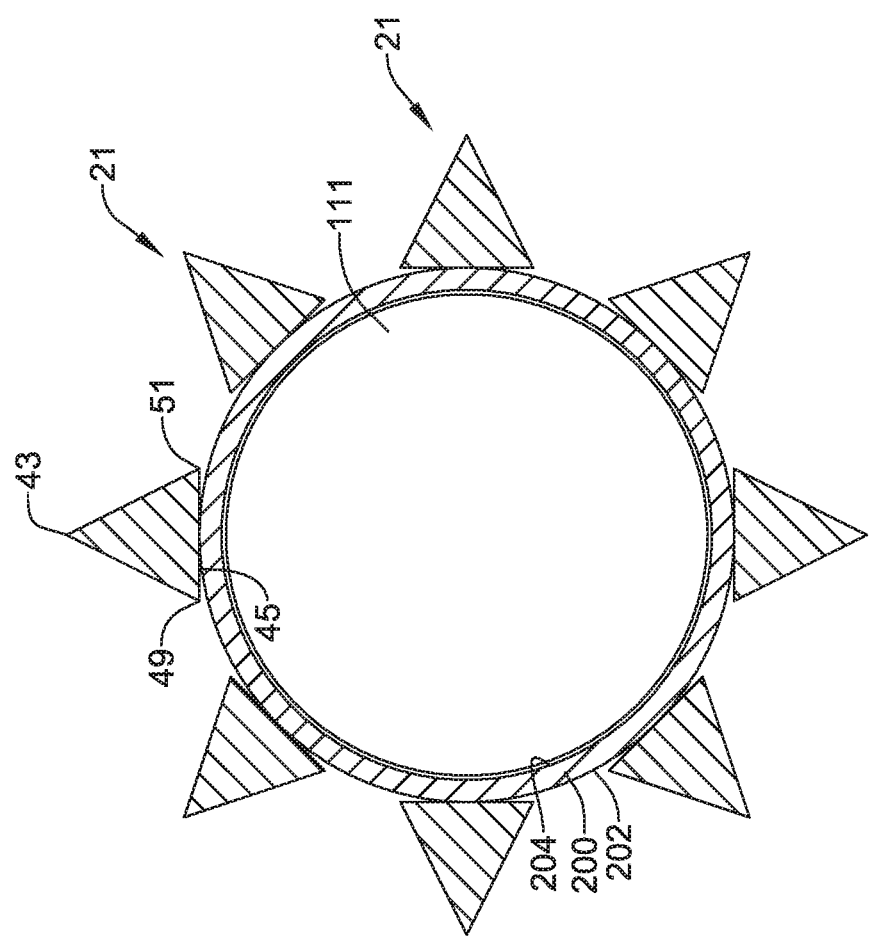

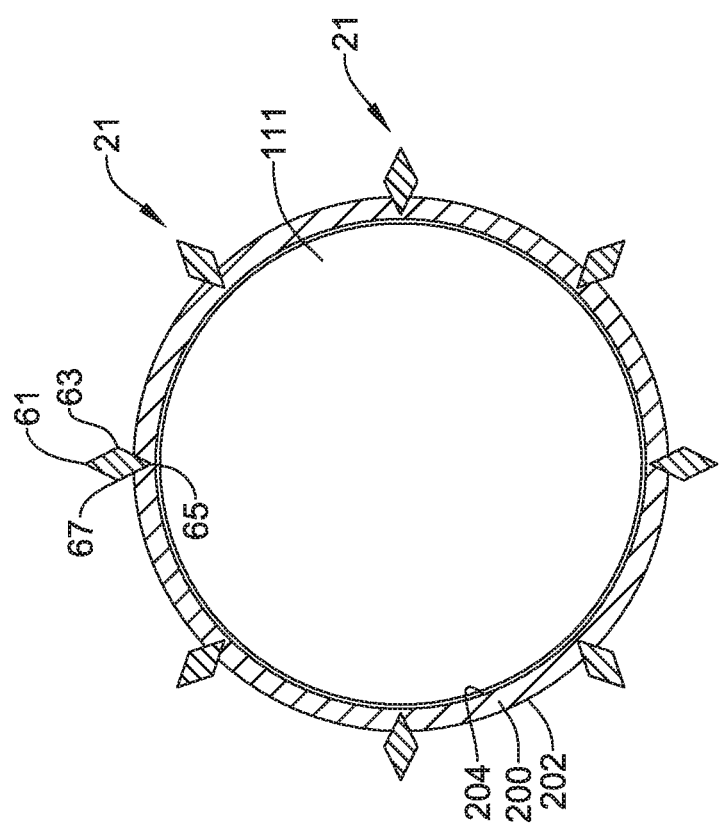

STENT WITH ANTI-MIGRATION FEATURES

CROSS-REFERENCE TO RELATED APPLICATIONS

This application claims priority under 35 U.S.C. § 119(e) to U.S. Provisional Application No. 62/127,486, filed Mar. 3, 2015, the entire disclosure of which is herein incorporated by reference.

TECHNICAL FIELD

The disclosure is directed to an endoprosthesis, such as a stent, including anti-migration features. More particularly, the disclosure is directed to an endoprosthesis, such as a stent, including wires with one or more projections.

BACKGROUND

An endoprosthesis may be configured to be positioned in a body lumen for a variety of medical applications. For example, an endoprosthesis may be used to treat a stenosis in a blood vessel, used to maintain a fluid opening or pathway in the vascular, urinary, biliary, tracheobronchial, esophageal or renal tracts, or to position a device such as an artificial valve or filter within a body lumen, in some instances. Bare or partially covered endoprostheses allow tissue ingrowth through the structure of the endoprosthesis to prevent migration of the endoprosthesis. However, if it is desired to remove the endoprosthesis at some later time, the ingrown tissue must be cut away, causing significant trauma to the body lumen. Fully covered endoprostheses, on the other hand, prevent tissue ingrowth to facilitate removal. However, fully covered endoprostheses are prone to migrate through the body lumen. Accordingly, it is desirable to provide endoprostheses that exhibit anti-migration features, while reducing the trauma to the body lumen of the patient if removal of the endoprosthesis is desired.

BRIEF SUMMARY

The disclosure is directed to several alternative designs, materials and methods of manufacturing medical device structures and assemblies, and uses thereof.

In one embodiment, an implantable medical device for implantation within a passageway of a patient comprises a framework including a plurality of wires. At least one of the plurality of wires may have a cross-section having a first tapered point. The implantable medical device may further comprise a covering layer having an inner diameter and an outer diameter. Additionally, the covering layer covers at least a portion of the framework, and the first tapered point may extend outward further than the outer diameter of the covering layer.

Additionally, or alternatively, in the above embodiment, the at least one of the plurality of wires may have a cross-section having a second tapered point.

Additionally, or alternatively, in any of the above embodiments, the second tapered point may extend inward further than the outer diameter of the covering layer Additionally, or alternatively, in any of the above embodiments, the second tapered point may extend inward further than the inner diameter of the covering layer.

Additionally, or alternatively, in any of the above embodiments, the cross-section of the at least one of the plurality of wires may further comprise a third tapered point.

Additionally, or alternatively, in any of the above embodiments, the cross-section of the at least one of the plurality of wires may be triangular.

Additionally, or alternatively, in any of the above embodiments, the at least one of the at least one of the plurality of wires may have a cross-section having a rectangular projection.

Additionally, or alternatively, in any of the above embodiments, the first tapered point may extend outward in a direction opposite the second tapered point.

Additionally, or alternatively, in any of the above embodiments, the second tapered point may be embedded into the covering layer.

Additionally, or alternatively, in any of the above embodiments, the covering layer may further have a central longitudinal axis, and wherein the first tapered point extends radially outward relative to the central longitudinal axis.

Additionally, or alternatively, in any of the above embodiments, at least one of the plurality of wires may be made from a Nickel Titanium alloy.

Additionally, or alternatively, in any of the above embodiments, the framework may be a self-expanding framework.

Additionally, or alternatively, in any of the above embodiments, the covering layer may be made from a biocompatible polymer.

Additionally, or alternatively, in any of the above embodiments, the covering layer may be flexible.

Additionally, or alternatively, in any of the above embodiments, wherein the first tapered point may extend outward from the outer diameter of the covering layer between 0.1 mm and 1.0 mm.

This disclosure also relates to a method of forming an implantable medical device comprising positioning a covering layer over a mandrel and weaving a plurality of wires over the covering layer to form a stent, the covering layer having a central longitudinal axis and an inner diameter and an outer diameter, and at least one of the plurality of wires having a cross-section including a first tapered point. In some embodiments, the plurality of wires are woven over the covering layer such that the first tapered point of the at least one of the plurality of wires extends outward away from the central longitudinal axis further than the outer diameter of the covering layer. In some embodiments, the method may further comprise removing the stent and the covering layer from the mandrel.

Additionally, or alternatively, in the above embodiment, wherein the at least one of the plurality of wires has a cross-section having a second tapered point, and further comprising embedding the second tapered point in the covering layer.

Additionally, or alternatively, in any of the above embodiments, the method may further comprise positioning the covering layer over a mandrel.

Additionally, or alternatively, in any of the above embodiments, the method may further comprise embedding the first tapered point in the covering layer.

Additionally, or alternatively, in any of the above embodiments, the at least one of the plurality of wires may have a cross-section having a second tapered point.

Additionally, or alternatively, in any of the above embodiments, the method may further comprise embedding the second tapered point in the covering layer.

Additionally, or alternatively, in any of the above embodiments, the second tapered point may extend inward further than the outer diameter of the covering layer.

Additionally, or alternatively, in any of the above embodiments, the second tapered point may extend inward further than the inner diameter of the covering layer.

Additionally, or alternatively, in any of the above embodiments, the first tapered point may extend outward in a direction opposite the second tapered point.

Additionally, or alternatively, in any of the above embodiments, the covering layer may be flexible.

Additionally, or alternatively, in any of the above embodiments, the covering layer may be a polymeric tubular member.

In another embodiment, a method of forming an implantable medical device may comprise weaving a plurality of wires to form a woven framework comprising a plurality of open cells, the framework having a central hollow region, at least one of the plurality of wires having a cross-section including a first tapered point. In some embodiments, the method may further comprise inserting a compliant filler into the central hollow region of the woven framework and covering the woven framework and the compliant filler with a cover material. Finally, the method may further comprise removing the compliant filler.

Additionally, or alternatively, in the above embodiment, the cover material may not adhere to the compliant filler.

Additionally, or alternatively, in any of the above embodiments, when the compliant filler is inserted into the central hollow region of the woven framework, an outer portion of the compliant filler may extend at least partially into one or more of the plurality of open cells.

Additionally, or alternatively, in any of the above embodiments, covering the woven framework and the compliant filler with a cover material may comprise one or more of: dipping the woven framework and the compliant filler in the cover material; spraying the cover material onto the woven framework and the compliant filler; and heat shrinking the cover material onto the woven framework and the compliant filler.

The above summary is not intended to describe each embodiment or every implementation of the present disclosure. Advantages and attainments, together with a more complete understanding of the disclosure, will become apparent and appreciated by referring to the following description and claims taken in conjunction with the accompanying drawings.

BRIEF DESCRIPTION OF THE DRAWINGS

The aspects of the disclosure may be further understood in consideration of the following detailed description of various embodiments in connection with the accompanying drawings, in which:

FIG. 1 is a schematic illustration of a patient showing a stent disposed within the patient's esophagus, in accordance with embodiments of the present disclosure;

FIG. 2 is a perspective view of an exemplary endoprosthesis, in accordance with embodiments of the present disclosure;

FIG. 3 is a view of a longitudinal cross-sectional configuration of the wires of the endoprosthesis of FIG. 2 as viewed along line 3-3;

FIG. 4 is a view of a transverse cross-sectional configuration of the endoprosthesis of FIG. 2 as viewed along line 4-4;

FIG. 5 is an alternative longitudinal cross-sectional configuration of the wires of the endoprosthesis of FIG. 2 taken along line 3-3;

FIG. 6 is an alternative transverse cross-sectional configuration of the wires of the endoprosthesis of FIG. 2 taken along line 4-4;

FIG. 7 is another alternative longitudinal cross-sectional configuration of the wires of the endoprosthesis of FIG. 2 taken along line 3-3;

FIG. 8 is another alternative transverse cross-sectional configuration of the wires of the endoprosthesis of FIG. 2 taken along line 4-4;

FIGS. 9A-9E are example cross-sections of wires of an endoprosthesis, in accordance with embodiments of the present disclosure;

FIG. 28 is an example cross-section of an endoprosthesis including a covering layer during forming of the endoprosthesis, in accordance with embodiments of the present disclosure;

FIGS. 29A and 29B are more example cross-sections of an endoprosthesis including a covering layer during forming of the endoprosthesis, in accordance with embodiments of the present disclosure.

Figure 10:
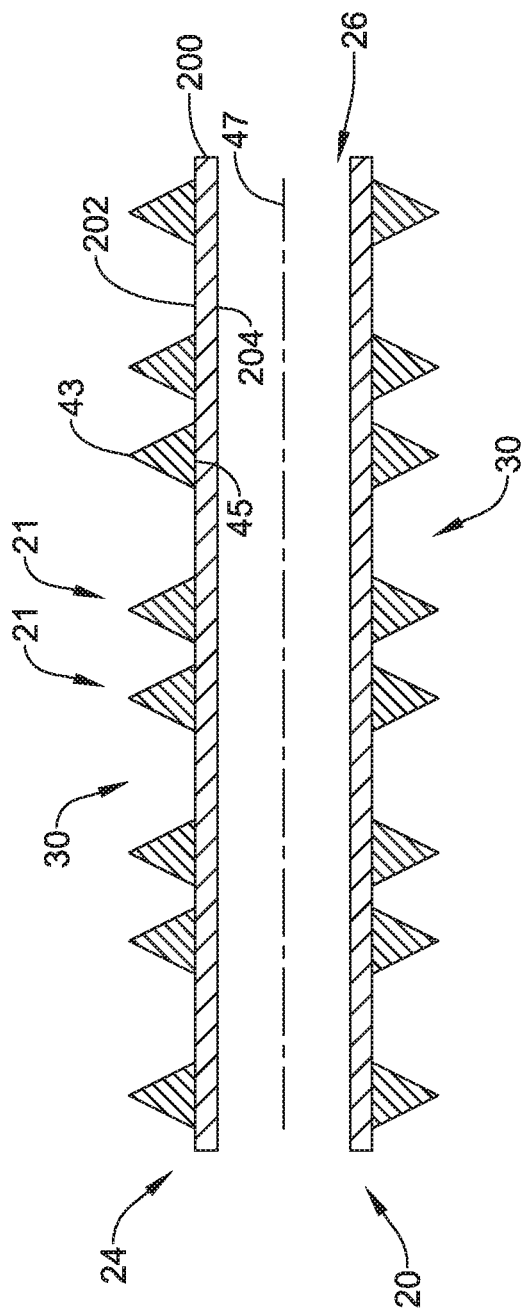
FIGS. 10-14 are example cross-sections of an endoprosthesis including a covering layer, in accordance with embodiments of the present disclosure.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

Definitions of certain terms are provided below and shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a," "an," and "the" include or otherwise refer to singular as well as plural referents, unless the content clearly dictates otherwise. As used in this specification and the appended claims, the term "or" is generally employed to include "and/or," unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

FIG. 1 provides a schematic illustration of the torso of a patient 10. The patient 10 includes an esophagus 14 leading to stomach 16. An endoprosthesis 18 may be seen in phantom, disposed within the esophagus 14. It will be appreciated that this placement is merely for illustrative purposes, as endoprosthesis 18 may be deployed elsewhere in esophagus 14. It will also be appreciated that while endoprosthesis 18 is described herein as an esophageal stent, endoprosthesis 18 may be deployed in a variety of other bodily lumens, including but not limited to the vascular, urinary, biliary, tracheobronchial, esophageal or renal tracts. Although illustrated as a stent, endoprosthesis 18 may be any of a number of devices that may be introduced endoscopically, subcutaneously, percutaneously or surgically to be positioned within an organ, tissue, or lumen, such as a heart, artery, vein, urethra, esophagus, trachea, bronchus, bile duct, or the like.

A difficulty in placing endoprosthesis 18 in esophagus 14 is that peristalsis of esophagus 14 may cause endoprosthesis 18 to migrate away from the initial implant site. Accordingly, in some embodiments, endoprosthesis 18 may be configured to help hold the endoprosthesis 18 in place within the esophagus 14. Endoprosthesis 18 may be held in place frictionally, for example between the walls of esophagus 14 and one or more features of endoprosthesis 18.

FIG. 2 illustrates an exemplary endoprosthesis 20. Endoprosthesis 20 may include a first end 24, a second end 26, and a woven wire framework 22, such as a stent, disposed about a longitudinal axis of endoprosthesis 20 that defines a lumen 28 extending therethrough. The term 'woven wire framework 22' may be referred to as 'wire framework 22' hereafter. The wire framework 22 may include one or more wires 21 which cross or otherwise interconnect to form a mesh-like structure of the wire framework 22, including a plurality of open cells 30. Wire framework 22 may be configured to transition from a compressed state to an expanded state.

Endoprosthesis 20 may be configured to be implanted in the vasculature of a patient, such as an aortic ostium, tortuous vessels, etc. In other embodiments, endoprosthesis 20 may be configured to be implanted in the urinary, biliary, tracheobronchial, esophageal or renal tracts, for example. Endoprosthesis 20, or a portion thereof, may be made from a biostable material, a bioabsorbable material, or a combination thereof. Examples of the biostable metal materials may include, but are not limited to, stainless steel, tantalum, tungsten, niobium, platinum, nickel-chromium alloys, cobalt-chromium alloys such as Elgiloy® and Phynox®, nitinol (e.g., 55% nickel, 45% titanium), and other alloys based on titanium, including nickel titanium alloys, or other suitable metals, or combinations or alloys thereof. Some suitable biostable polymeric materials include, but are not necessarily limited to, polyamide, polyether block amide, polyethylene, polyethylene terephthalate, polypropylene, polyvinylchloride, polyurethane, polytetrafluoroethylene, polysulfone, and copolymers, blends, mixtures or combinations thereof. Examples of suitable bioabsorbable materials may include polymers, such as poly-L-lactide (PLLA), polyglycolide (PGA), polylactide (PLA), poly-D-lactide (PDLA), polycaprolactone, polydioxanone, polygluconate, polylactic acid-polyethylene oxide copolymers, modified cellulose, collagen, poly(hydroxybutyrate), polyanhydride, polyphosphoester, poly(amino acids), and combinations thereof.

FIGS. 3 and 4 depict example cross-sectional configurations of the wires of an example endoprosthesis 20 taken along lines 3-3 and 4-4 of FIG. 2, respectively. FIG. 3 depicts endoprosthesis 20 having a central longitudinal axis 47 running through the center of endoprosthesis 20. Additionally, in the embodiments of FIGS. 3 and 4, the one or more wires 21 of endoprosthesis 20 may have a cross-section including a first tapered point 43. In at least some embodiments, first tapered point 43 may extend generally away from central longitudinal axis 47. Although in FIGS. 3 and 4, first tapered point 43 is depicted generally extending perpendicularly to central longitudinal axis 47, in other embodiments, first tapered point 43 may be disposed rotated with respect to central longitudinal axis 47 such that there may be an angle anywhere between greater than 0 degrees and less than 90 degrees between central longitudinal axis 47 and a line extending from first tapered point 43 in the direction of the taper. In other embodiments, the range of the angle may be between 15 degrees and 75 degrees or between 30 degrees and 60 degrees, for example, and in some particular examples, the angle may be about 35 degrees, about 45 degrees, or about 55 degrees, for instance.

Additionally, in some embodiments, the cross-section of the one or more wires 21 may have one or more additional tapered points, such as a second tapered point 49. Second tapered point 49 may generally extend outward from the center of the cross-section of the one or more wires 21 in a direction different than first tapered point 43. In some further embodiments, the cross-section of the one or more wires 21 may include one or more additional tapered points, such as a third tapered point 51, which may generally extend outward from the center of the cross-section of the one or more wires 21 in a direction different than either of first tapered point 43 and second tapered point 49. In at least some of these embodiments, the cross-section of the one or more wires 21 including tapered points 43, 49, and 51 may form a triangle shape. However, in other embodiments, the cross-section of the one or more wires 21 may form other shapes. Additionally, as depicted in FIGS. 3 and 4, tapered points 49 and 51 extend generally parallel to central longitudinal axis 47, causing face 45 to be generally parallel to central longitudinal axis 47, in other examples, the one or more wires 21 may be rotated in any manner with respect to central longitudinal axis 47 that face 45 may extend at any angle with respect to central longitudinal axis 47.

FIGS. 5 and 6 depict additional alternative cross-sectional configurations of the wires of an example endoprosthesis 20 taken along lines 3-3 and 4-4 of FIG. 2, respectively. FIG. 5 depicts endoprosthesis 20 having a central longitudinal axis 47 running through the center of endoprosthesis 20. Additionally, in the embodiments of FIGS. 5 and 6, the one or more wires 21 of endoprosthesis 20 may have a cross-section including at least a first tapered point 61 and a second tapered point 65. In at least some embodiments, first tapered point 61 may extend generally away from the center of the cross-section of the one or more wires 21 in a first direction and second tapered point 65 may extend generally away from the center of the cross-section of the one or more wires 21 in a second direction that is generally opposite the first direction, although in other embodiments this is not required. Additionally, first tapered point 61 may extend generally away from central longitudinal axis 47 while second tapered point 65 may extend generally toward central longitudinal axis 47. As depicted in FIGS. 5 and 6, first and second tapered points 61, 65 extend generally perpendicular to central longitudinal axis 47, however, in other examples, the one or more wires 21 may be rotated such that first and second tapered points 61, 65 extend at any angle with respect to central longitudinal axis 47.

Additionally, in some embodiments, the cross-section of the one or more wires 21 may further include one or more additional tapered points, such as third and fourth tapered points 63, 67. Third and fourth tapered points 63, 67 may generally extend outward from the center of the cross-section of the one or more wires 21 in third and fourth directions, which may be different than the first and second directions. The third and fourth directions may generally be opposite, but this is not required in all embodiments. In at least some of these embodiments, the cross-section of the one or more wires 21 including tapered points 61, 63, 65, and 67 may form a diamond shape. However, in other embodiments, the cross-section of the one or more wires 21 may form other shapes. Additionally, as depicted in FIGS. 5 and 6, third and fourth tapered points 63 and 67 extend generally parallel to central longitudinal axis 47, in other examples, the one or more wires 21 may be rotated in any manner with respect to central longitudinal axis 47 that third and fourth tapered points 63, 67 may extend at any angle with respect to central longitudinal axis 47.

FIGS. 7 and 8 depict additional alternative cross-sectional configurations of the wires of an example endoprosthesis 20 taken along lines 3-3 and 4-4 of FIG. 2, respectively. FIG. 7 depicts endoprosthesis 20 having a central longitudinal axis 47 running through the center of endoprosthesis 20. Additionally, in the embodiments of FIGS. 7 and 8, the one or more wires 21 of endoprosthesis 20 may have a cross-section including at least a first tapered point 71, a second tapered point 75, and a first projection 73. In at least some embodiments, first tapered point 71 may extend generally away from the center of the cross-section of the one or more wires 21 in a first direction and second tapered point 75 may extend generally away from the center of the cross-section of the one or more wires 21 in a second direction that is generally opposite the first direction. Additionally, first tapered point 71 may extend generally away from central longitudinal axis 47 while second tapered point 75 may extend generally toward central longitudinal axis 47. As depicted in FIGS. 7 and 8, first and second tapered points 71, 75 extend generally perpendicular to central longitudinal axis 47, however, in other examples, the one or more wires 21 may be rotated such that first and second tapered points 71, 75 extend at any angle with respect to central longitudinal axis 47. Further, first projection 73 may generally extend outward from the center of the cross-section of wire 21 in a third direction that is different than both the first and second directions. In some embodiments, first projection 73 may be a generally squared shaped, however, in other embodiments, first projection 73 may be round, or trapezoidal, or any other suitable shape.

Additionally, in some embodiments, the cross-section of the one or more wires 21 may further include one or more additional projections, such as a second projection 77. Second projection 77 may generally extend outward from the center of the cross-section the one or more wires 21 in a fourth direction that is different than any of the first, second, and third directions. Additionally, in some embodiments, the fourth direction may general be opposite the third direction, although this is not required. Although the third and fourth directions depicted in FIGS. 7 and 8 are generally parallel to central longitudinal axis 47, in other embodiments the one or more wires 21 may be disposed rotated with respect to central longitudinal axis 47 such that the third and fourth directions are disposed at any angle with respect to central longitudinal axis 47. Additionally, as with first projection 73, second projection 77 may be general squared shaped. However, in other embodiments, second projection 77 may be round, or trapezoidal, or any other suitable shape, and may be differently shaped than first projection 73.

FIGS. 9A-9E depict additional example cross-sectional shapes that the one or more wires 21 may have. FIG. 9A depicts a parallelogram 91. Parallelogram 91 may have four sides 92a-92d, where sides 92a and 92b may be of the same length and sides 92c and 92d may be of the same length, with the length of sides 92a and 92b being different than the length of sides 92c and 92d. Side 92a may intersect with sides 92c and 92d to form angles Y and X, respectively. Similarly, side 92b may intersect with sides 92c and 92d to form angles X and Y, respectively. FIG. 9B depicts square 93 having four equal length sides 94. Each intersection of two sides 94 may form right angles Z. FIG. 9C depicts rhombus 95. Rhombus 95 includes four equal length sides 96. In contrast to square 94, sides 96 may intersect with each other as depicted to form two different angles, angles A and B.

FIG. 9D depicts trapezoid 97. Trapezoid 97 has four sides 98a-98d, in which at least one side has a length different than the other sides. As depicted, side 98a may intersect with side 98b to form obtuse angle D, and side 98b may intersect with side 98c to form acute angle E. Side 98c may intersect with side 98d to form acute angle F, and side 98d may intersect with side 98a to form obtuse angle C. Additionally, sides 98a and 98c may be disposed parallel to each other such that a line drawn perpendicular to side 98a intersects side 98c at a right angle G. FIG. 9E depicts kite 99. Kite 99 includes two sides 100 and two sides 102, where sides 100 are of equal length, and sides 102 are of an equal length that is different than the length of sides 100. Sides 100 may intersect with sides 102 to form angles H. Sides 100 may intersect with each other to form angle I, and sides 102 may intersect with each other to form angle J. Additionally, lines drawn between the corners of the intersection of sides 100, sides 102, and both intersections of sides 100 and 102 may cross each other at a right angle, as indicated in FIG. 9E.

In some embodiments, endoprosthesis 20 may further include a covering layer, such as a polymeric layer, covering the wires 21 of the endoprosthesis 20, such as a portion of the wires 21 or the entire endoprosthesis 20. In some embodiments, the covering layer, e.g., polymeric layer, may be disposed at least partially around the one or more wires 21. However, in other embodiments, the one or more wires 21 may be disposed at least partially around the covering layer, e.g., polymeric layer. In general, the covering layer may be formed of any desired material, such as a textile material, a polymeric material, or other material. For example, the covering layer, in the form of a polymeric layer, may be formed of any desired polymeric material in order to give endoprosthesis 20 any desired properties. In some embodiments, the polymeric layer may be formed of a biocompatible material such as polyurethane or silicone. In some examples, the polymeric layer may have a thickness between 0.1 mm and 1.5 mm, or between 0.3 mm and 1.3 mm, and in some instances may be 0.5 mm, 1.0 mm, or 1.25 mm thick.

FIGS. 10-14 depict example cross-sectional views of endoprosthesis 20 including both one or more wires 21 forming a framework and covering layer 200 covering the framework. As depicted in FIGS. 10-14, covering layer 200 may have both an outer wall surface 202 and an inner wall surface 204. In the embodiment of FIG. 10, endoprosthesis 20 may have one or more wires 21 with a cross-section similar to that described with respect to FIGS. 3 and 4, including at least a first tapered point 43. Additionally, in the embodiment of FIG. 10, the covering layer 200 may cover the framework such that the one or more wires 21 may be disposed completely around covering layer 200. For example, the entirety of the one or more wires 21 may be disposed radially further away from central longitudinal axis 47 than outer wall surface 202 of covering layer 200. Accordingly, faces 45 may be disposed in contact with outer wall surface 202 of covering layer 200. In some embodiments, the one or more wires 21 may be glued or otherwise secured to outer wall surface 202 of covering layer 200, but this is not required. As described with respect to previous FIGS., although FIG. 10 depicts faces 45 as generally parallel to central longitudinal axis 47, in other embodiments, the one or more wires 21 may be disposed rotated with respect to central longitudinal axis 47 such that faces 45 extend at any angle with respect to central longitudinal axis 47.

Figure 11:
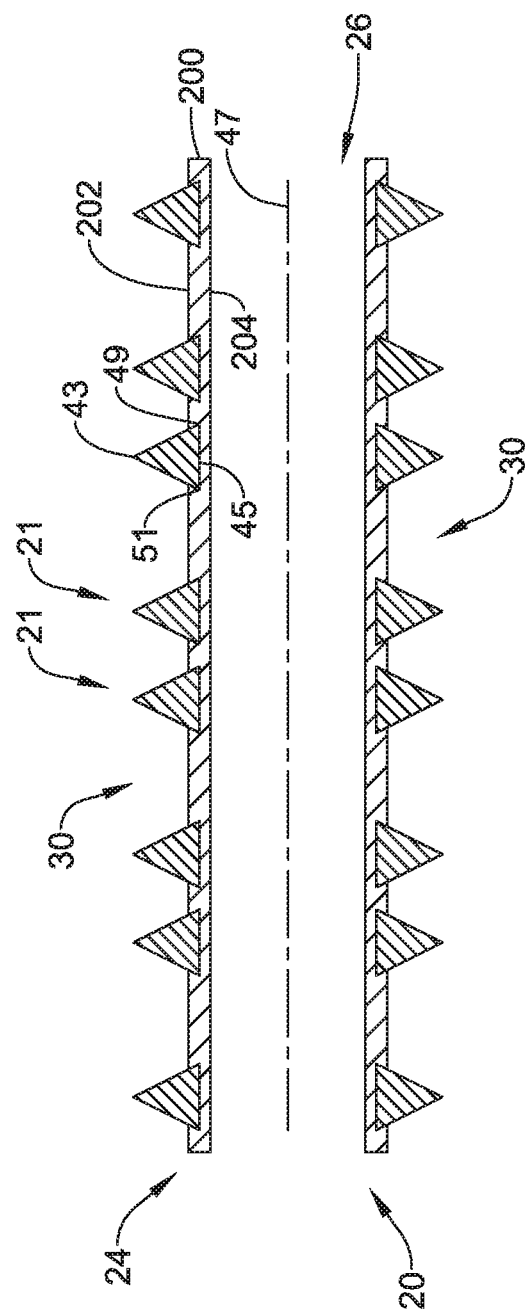

In the embodiment of FIG. 11, the covering layer 200 may cover the framework such that the one or more wires 21 may only be partially disposed around covering layer 200. For instance, first tapered points 43 may be disposed radially further away from central longitudinal axis 47 than outer wall surface 202 of covering layer 200. However, outer wall surface 202 of covering layer 200 may be disposed radially further away from central longitudinal axis 47 than second and third tapered points 49, 51. However, second and third tapered points 49, 51 may still be disposed radially further away from central longitudinal axis 47 than inner wall surface 204 of covering layer 200. In such embodiments, second and third tapered points 49, 51 may be embedded within covering layer 200. Although FIG. 11 depicts both second and third tapered points 49, 51 embedded within covering layer 200, in other embodiments only one of second and third tapered points 49, 51 may be embedded within covering layer 200. In such embodiments, the other of second and third tapered points 49, 51 may be disposed radially further away from central longitudinal axis 47 than outer wall surface 202 of covering layer 200. Additionally, although FIG. 11 depicts faces 45 as generally parallel to central longitudinal axis 47, in other embodiments, the one or more wires 21 may be disposed rotated with respect to central longitudinal axis 47 such that faces 45 extend at any angle with respect to central longitudinal axis 47.

Figure 12:
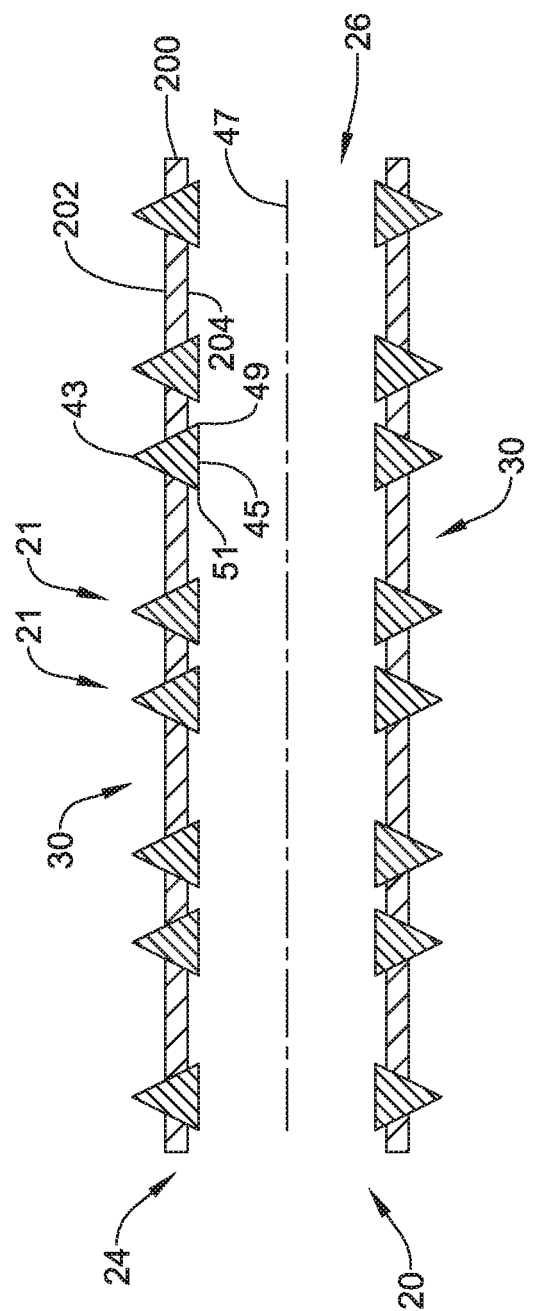

In the embodiment of FIG. 12, the covering layer 200 may cover the framework such that at least a portion of the one or more wires 21 may be disposed radially closer to central longitudinal axis 47 than inner wall surface 204 of covering layer 200 while at least a portion of the one or more wires 21 may be disposed radially further away from central longitudinal axis 47 than outer wall surface 202 of covering layer 200. For instance, first tapered points 43 may be disposed radially further away from central longitudinal axis 47 than outer wall surface 202 of covering layer 200, while second and third tapered points 49, 51 may be disposed radially closer to central longitudinal axis 47 than inner wall surface 204 of covering layer 200. In these embodiments, covering layer 200 may be disposed in open cells 30 between the one or more wires 21. Further, although depicted in FIG. 12 with both second and third tapered points 49, 51 disposed radially closer to central longitudinal axis 47 than inner wall surface 204 of covering layer 200, in other embodiments, only one of second and third tapered points 49, 51 may be disposed radially closer to central longitudinal axis 47 than inner wall surface 204 of covering layer 200. In these examples, the other of second and third tapered points 49, 51 may be embedded within covering layer 200 or disposed radially further away from central longitudinal axis 47 than outer wall surface 202 of covering layer 200. Additionally, although FIG. 12 depicts faces 45 as generally parallel to central longitudinal axis 47, in other embodiments, the one or more wires 21 may be disposed rotated with respect to central longitudinal axis 47 such that faces 45 extend at any angle with respect to central longitudinal axis 47.

Figure 13:
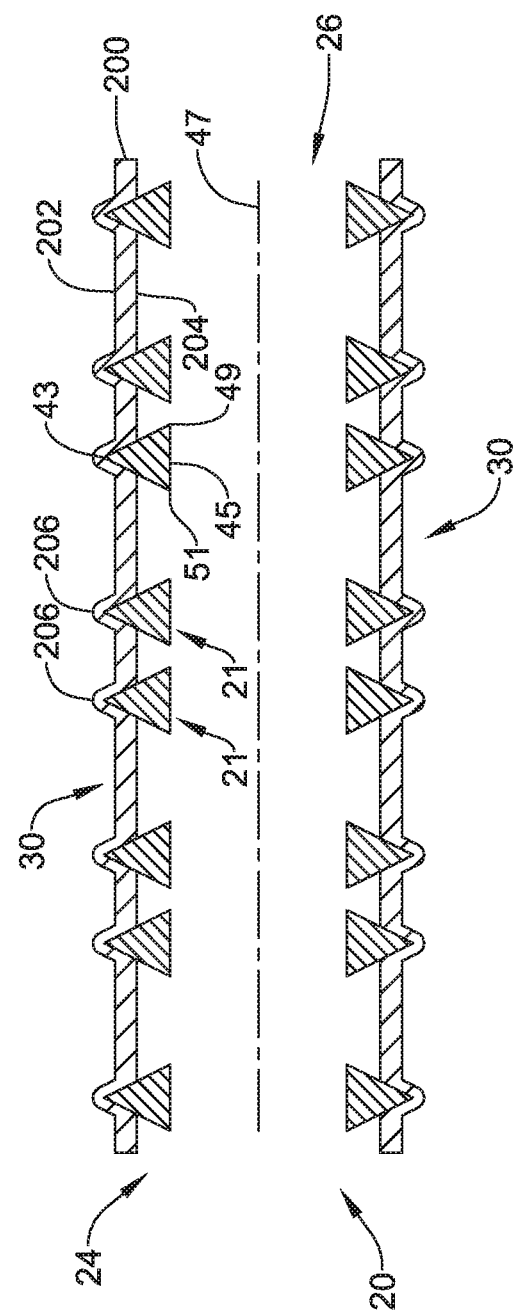

In the embodiment of FIG. 13, the covering layer 200 may cover the framework such that covering layer 200 may disposed at least partially around the one or more wires 21. For instance, outer wall surface 202 of covering layer 200 may be disposed radially further away from central longitudinal axis 47 than first tapered points 43 where first tapered points 43 contact covering layer 200. However, in at least some of these embodiments, first tapered points 43 may be disposed radially further away from central longitudinal axis 47 than inner wall surface 204 of covering layer 200. In these embodiments, first tapered points 43 may be embedded within covering layer 200. Additionally in these embodiments, second and third tapered points 49, 51 may be disposed radially closer to central longitudinal axis 47 than inner wall surface 204 of covering layer 200. Although, in some embodiments, only one of second and third tapered points 49, 51 may be disposed radially closer to central longitudinal axis 47 than inner wall surface 204 of covering layer 200. The other of second and third tapered points 49, 51 may be disposed radially further away from central longitudinal axis 47 than inner wall surface 204 of covering layer 200 and embedded within covering layer 200. In these embodiments, covering layer 200 may be disposed at least partially in open cells 30 between the one or more wires 21. In some of these embodiments, outer wall surface 202 of covering layer 200 may include bumps 206 where first tapered points 43 are embedded within covering layer 200 (and may include additional bumps 206 in embodiments where other tapered points are embedded within covering layer 200). Additionally, although FIG. 13 depicts faces 45 as generally parallel to central longitudinal axis 47, in other embodiments, the one or more wires 21 may be disposed rotated with respect to central longitudinal axis 47 such that faces 45 extend at any angle with respect to central longitudinal axis 47.

Figure 14:
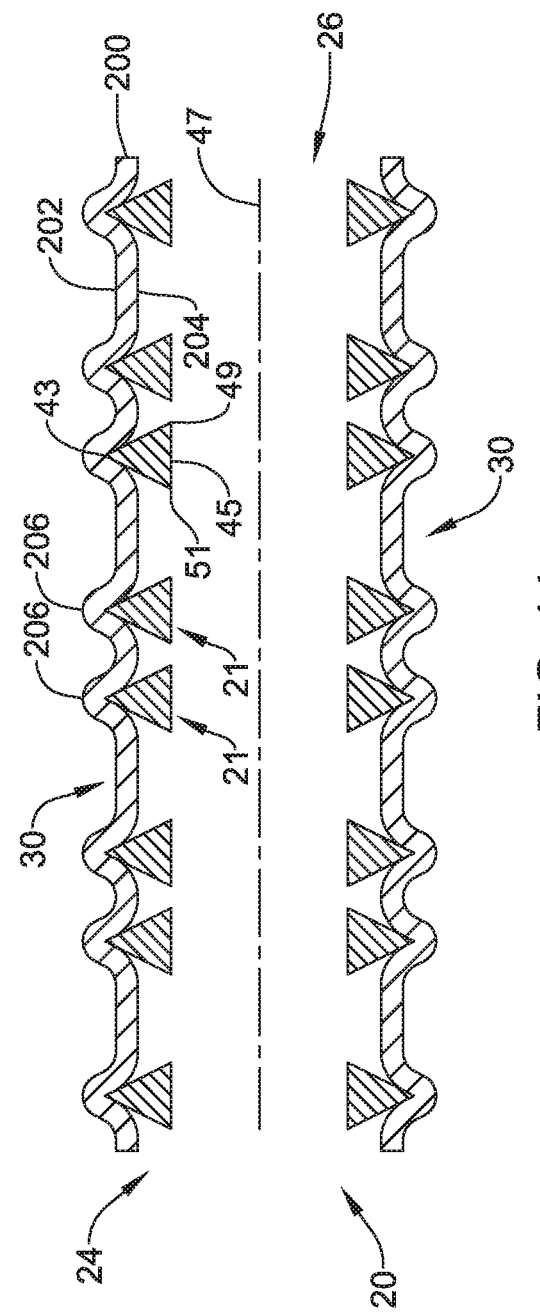

In the embodiment of FIG. 14, the covering layer 200 may cover the framework such that the entirety of covering layer 200 may be disposed completely over the one or more wires 21. For instance, both outer wall surface 202 and inner wall surface 204 of covering layer 200 may be disposed radially further away from central longitudinal axis 47 than all of the one or more wires 21, including first tapered points 43, where the one or more wires 21 contact covering layer 200 at any cross-section perpendicular to the longitudinal axis 47. In these embodiments, covering layer 200 may be disposed at least partially in open cells 30 between the one or more wires 21. In some of these embodiments, outer wall surface 202 of covering layer 200 may include bumps 206 proximate first tapered points 43. Additionally, although FIG. 14 depicts faces 45 as generally parallel to central longitudinal axis 47, in other embodiments, the one or more wires 21 may be disposed rotated with respect to central longitudinal axis 47 such that faces 45 extend at any angle with respect to central longitudinal axis 47.

Figure 15:
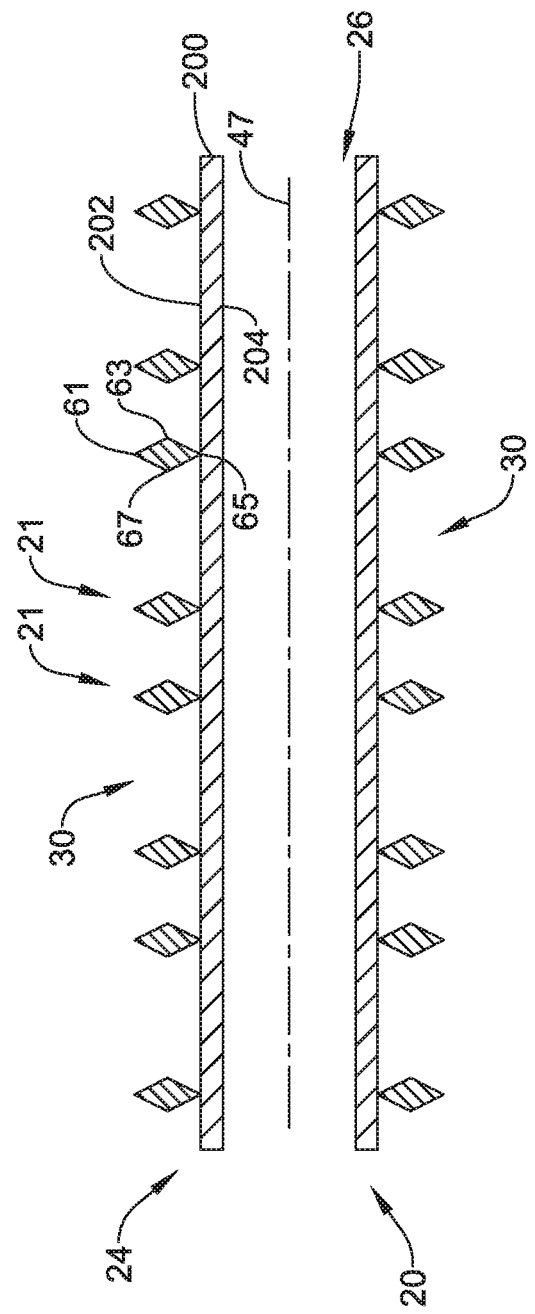
FIGS. 15-19 are example cross-sections of an endoprosthesis including a covering layer, in accordance with embodiments of the present disclosure.

FIGS. 15-19 depict additional alternative cross-sectional views of endoprosthesis 20 including both one or more wires 21 forming a framework and covering layer 200 covering the framework. As depicted in FIGS. 15-19, covering layer 200 may have both an outer wall surface 202 and an inner wall surface 204. In the embodiment of FIG. 15, endoprosthesis 20 may have one or more wires 21 with a cross-section similar to that described with respect to FIGS. 5 and 6, including at least a first tapered point 61 and a second tapered point 65. Additionally, in the embodiment of FIG. 15, the covering layer 200 may cover the framework such that the one or more wires 21 may be disposed completely around covering layer 200. For example, the entirety of the one or more wires 21 may be disposed radially further away from central longitudinal axis 47 than outer wall surface 202 of covering layer 200. However, the one or more wires 21 may be disposed in contact with outer wall surface 202 of covering layer 200. In some embodiments, the one or more wires 21 may be glued or otherwise secured to outer wall surface 202 of covering layer 200, but this is not required. As described with respect to previous FIGS., although FIG. 15 depicts first and second tapered points 61, 65 as extending generally perpendicular to central longitudinal axis 47, in other embodiments, the one or more wires 21 may be disposed rotated with respect to central longitudinal axis 47 such that first and second tapered points 61, 65 extend at any angle with respect to central longitudinal axis 47.

Figure 16:
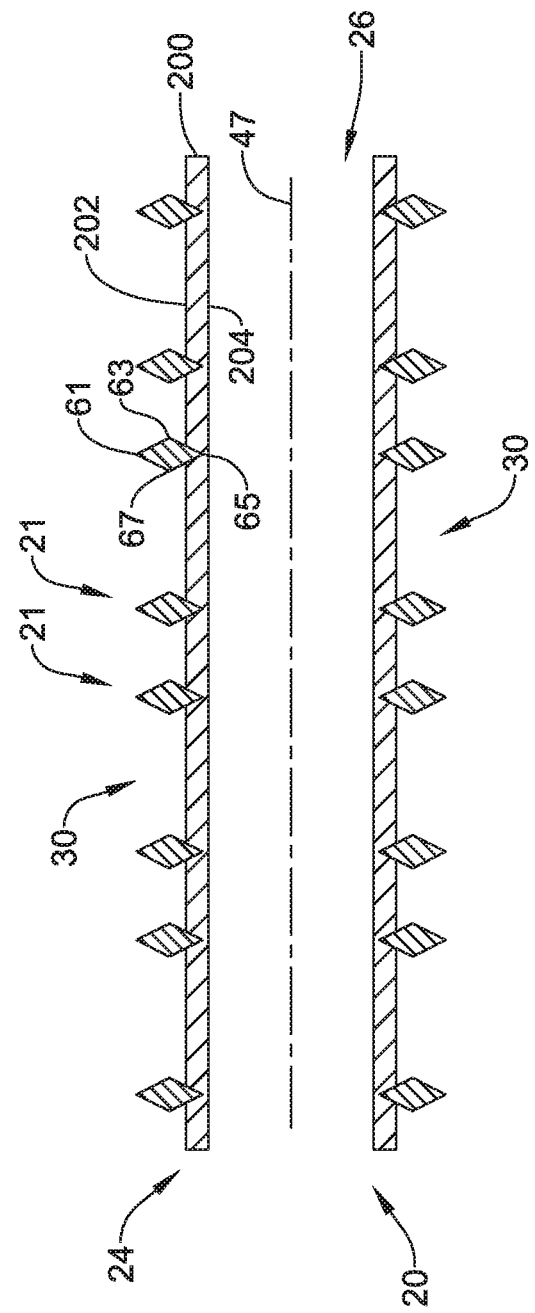

In the embodiment of FIG. 16, the covering layer 200 may cover the framework such that the one or more wires 21 may only be partially disposed around covering layer 200. For instance, first tapered points 61 may be disposed radially further away from central longitudinal axis 47 than outer wall surface 202 of covering layer 200. However, outer wall surface 202 of covering layer 200 may be disposed radially further away from central longitudinal axis 47 than second tapered points 65. In some embodiments, second tapered points 65 may still be disposed radially further away from central longitudinal axis 47 than inner wall surface 204 of covering layer 200. In such embodiments, second tapered points 65 may be embedded within covering layer 200. Although FIG. 16 depicts both third and fourth tapered points 63, 67 disposed radially further away from central longitudinal axis 47 than outer wall surface 202 of covering layer 200, in other embodiments one or more of third and fourth tapered points 63, 67 may be embedded within covering layer 200. In these embodiments, covering layer 200 may be disposed at least partially in open cells 30 between the one or more wires 21. Additionally, although FIG. 16 depicts first and second tapered points 61, 65 as extending generally perpendicular to central longitudinal axis 47, in other embodiments, the one or more wires 21 may be disposed rotated with respect to central longitudinal axis 47 such that first and second tapered points 61, 65 extend at any angle with respect to central longitudinal axis 47.

Figure 17:
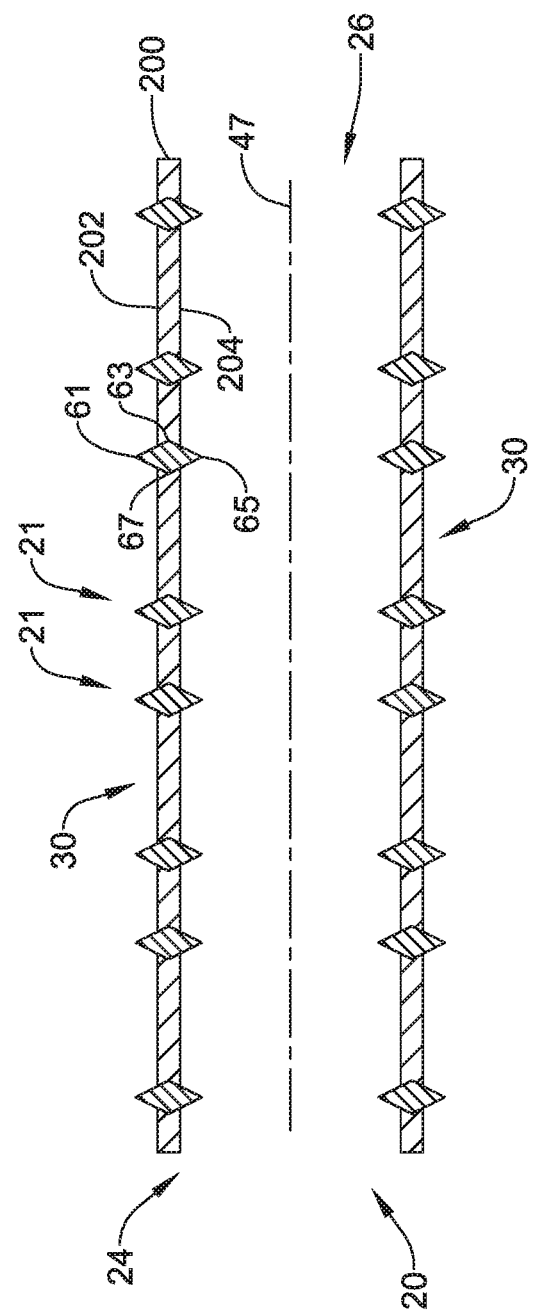

In the embodiment of FIG. 17, the covering layer 200 may cover the framework such that at least a portion of the one or more wires 21 may be disposed radially closer to central longitudinal axis 47 than inner wall surface 204 of covering layer 200 while at least a portion of the one or more wires 21 may be disposed radially further away from central longitudinal axis 47 than outer wall surface 202 of covering layer 200. For instance, first tapered points 61 may be disposed radially further away from central longitudinal axis 47 than outer wall surface 202 of covering layer 200, while second tapered points 65 may be disposed radially closer to central longitudinal axis 47 than inner wall surface 204 of covering layer 200. In these embodiments, covering layer 200 may be disposed in open cells 30 between the one or more wires 21. Further, although depicted in FIG. 17 with both third and fourth tapered points 63, 67 embedded within covering layer 200, in other embodiments only one of third and fourth tapered points 63, 67 may be embedded with the other of third and fourth tapered points 63, 67 disposed either radially closer to central longitudinal axis 47 than inner wall surface 204 of covering layer 200 or radially further away from central longitudinal axis 47 than outer wall surface 202 of covering layer 200. Additionally, although FIG. 17 depicts first and second tapered points 61, 65 as extending generally perpendicular to central longitudinal axis 47, in other embodiments, the one or more wires 21 may be disposed rotated with respect to central longitudinal axis 47 such that first and second tapered points 61, 65 extend at any angle with respect to central longitudinal axis 47.

Figure 18:
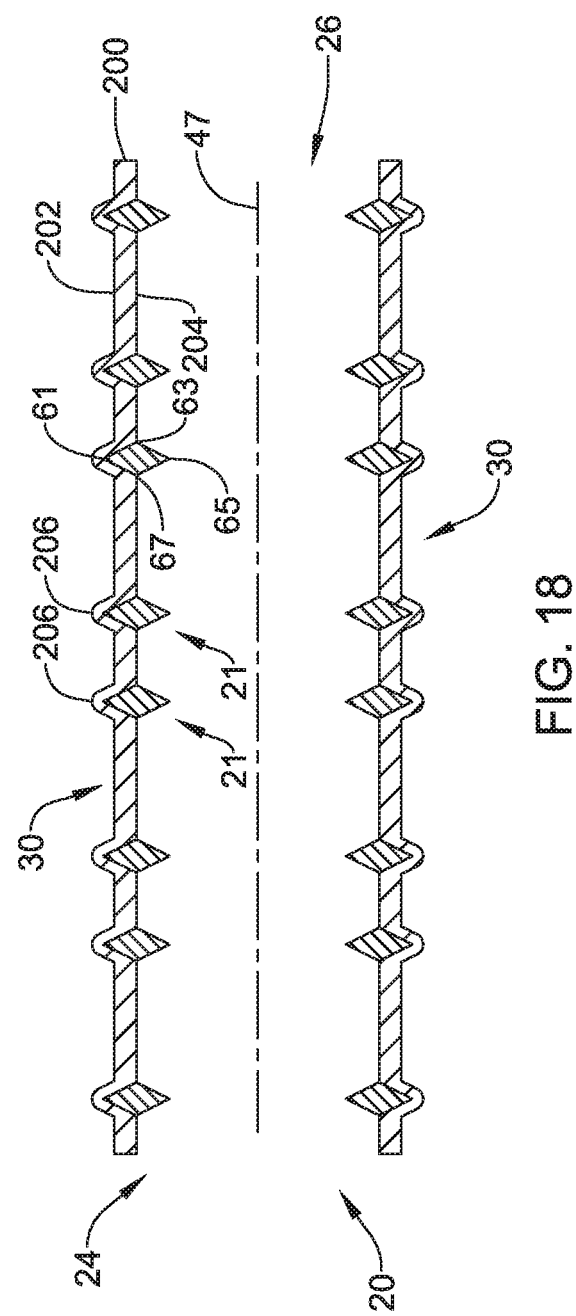

In the embodiment of FIG. 18, the covering layer 200 may cover the framework such that covering layer 200 may disposed at least partially around the one or more wires 21. For instance, outer wall surface 202 of covering layer 200 may be disposed radially further away from central longitudinal axis 47 than first tapered points 61 where first tapered points 61 contact covering layer 200. However, in at least some of these embodiments, first tapered points 61 may be disposed radially further away from central longitudinal axis 47 than inner wall surface 204 of covering layer 200. In these embodiments, first tapered points 61 may be embedded within covering layer 200. Further, although depicted in FIG. 18 with both third and fourth tapered points 63, 67 embedded within covering layer 200, in other embodiments only one of third and fourth tapered points 63, 67 may be embedded with the other of third and fourth tapered points 63, 67 disposed either radially closer to central longitudinal axis 47 than inner wall surface 204 of covering layer 200 or radially further away from central longitudinal axis 47 than outer wall surface 202 of covering layer 200. In these embodiments, covering layer 200 may be disposed at least partially in open cells 30 between the one or more wires 21. In some of these embodiments, outer wall surface 202 of covering layer 200 may include bumps 206 where first tapered points 61 are embedded within covering layer 200 (and may include additional bumps 206 in embodiments where other tapered points are embedded within covering layer 200). Additionally, although FIG. 18 depicts first and second tapered points 61, 65 as extending generally perpendicular to central longitudinal axis 47, in other embodiments, the one or more wires 21 may be disposed rotated with respect to central longitudinal axis 47 such that first and second tapered points 61, 65 extend at any angle with respect to central longitudinal axis 47.

Figure 19:
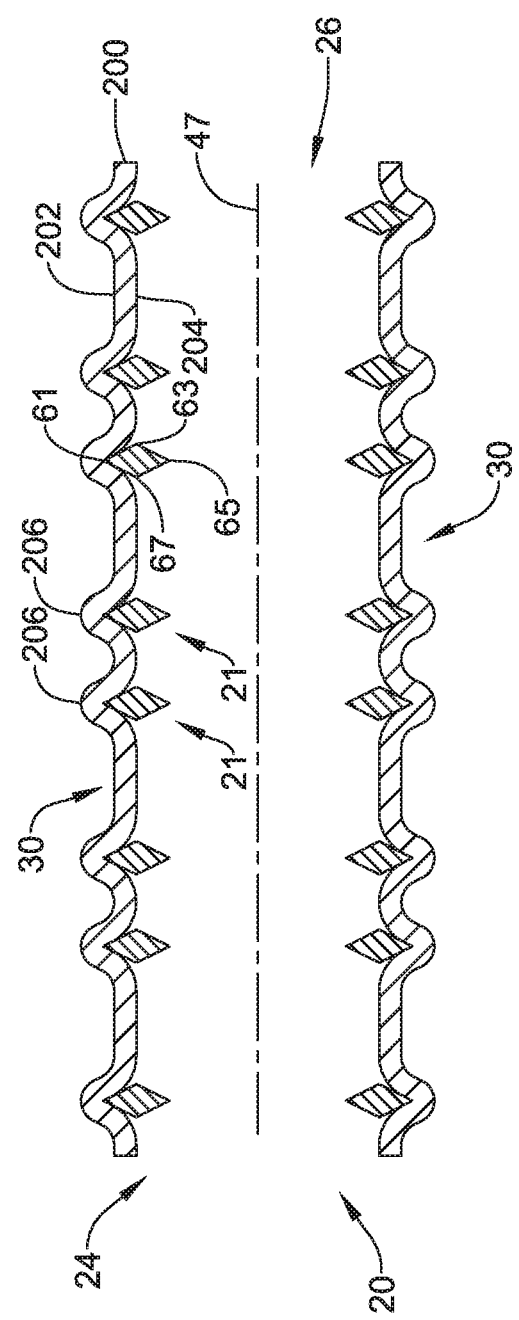

In the embodiment of FIG. 19, the covering layer 200 may cover the framework such that the entirety of covering layer 200 may disposed completely over the one or more wires 21. For instance, both outer wall surface 202 and inner wall surface 204 of covering layer 200 may be disposed radially further away from central longitudinal axis 47 than all of the one or more wires 21, including first tapered points 61, where the one or more wires 21 contact covering layer 200 at any cross-section perpendicular to the longitudinal axis 47. In these embodiments, covering layer 200 may be disposed at least partially in open cells 30 between the one or more wires 21. In some of these embodiments, outer wall surface 202 of covering layer 200 may include bumps 206 proximate first tapered points 61. Additionally, although FIG. 19 depicts first and second tapered points 61, 65 as extending generally perpendicular to central longitudinal axis 47, in other embodiments, the one or more wires 21 may be disposed rotated with respect to central longitudinal axis 47 such that first and second tapered points 61, 65 extend at any angle with respect to central longitudinal axis 47.

Figure 20:
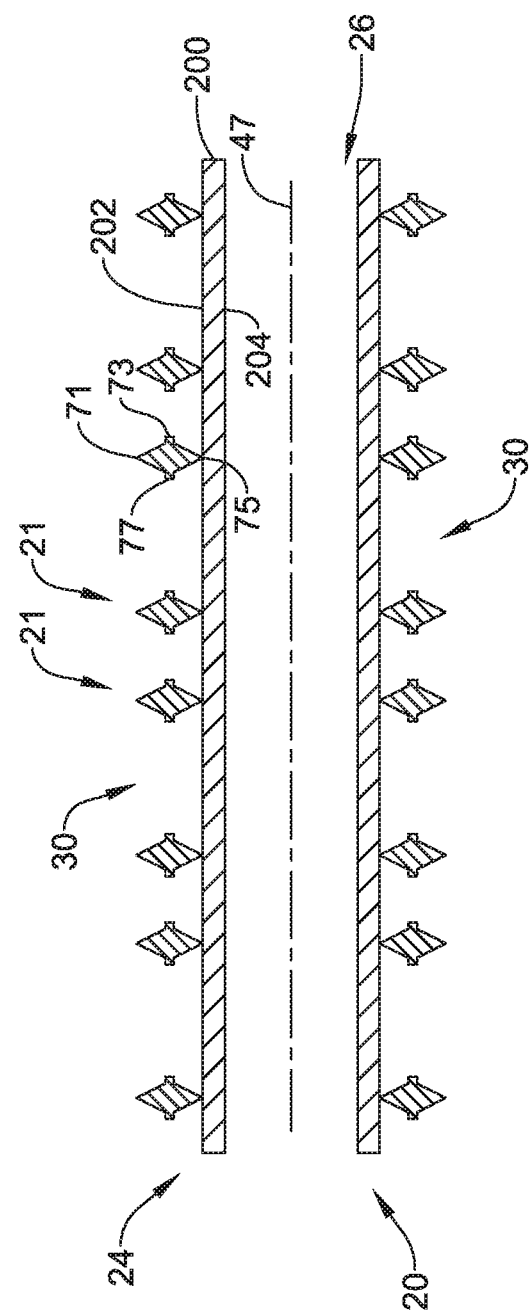
FIGS. 20-24 are example cross-sections of an endoprosthesis including a covering layer, in accordance with embodiments of the present disclosure.

FIGS. 20-24 depict additional alternative cross-sectional views of endoprosthesis 20 including both one or more wires 21 forming a framework and covering layer 200 covering the framework. As depicted in FIGS. 20-24, covering layer 200 may have both an outer wall surface 202 and an inner wall surface 204. In the embodiment of FIG. 20, endoprosthesis 20 may have one or more wires 21 with a cross-section similar to that described with respect to FIGS. 7 and 8, including at least a first tapered point 71, a second tapered point 75, and a first projection 73. Additionally, in the embodiment of FIG. 20, the covering layer 200 may cover the framework such that the one or more wires 21 may be disposed completely around covering layer 200. For example, the entirety of the one or more wires 21 may be disposed radially further away from central longitudinal axis 47 than outer wall surface 202 of covering layer 200. However, the one or more wires 21 may be disposed in contact with outer wall surface 202 of covering layer 200. In some embodiments, the one or more wires 21 may be glued or otherwise secured to outer wall surface 202 of covering layer 200, but this is not required. As described with respect to previous FIGS., although FIG. 20 depicts first and second tapered points 71, 75 as extending generally perpendicular to central longitudinal axis 47, in other embodiments, the one or more wires 21 may be disposed rotated with respect to central longitudinal axis 47 such that first and second tapered points 71, 75 extend at any angle with respect to central longitudinal axis 47.

Figure 21:
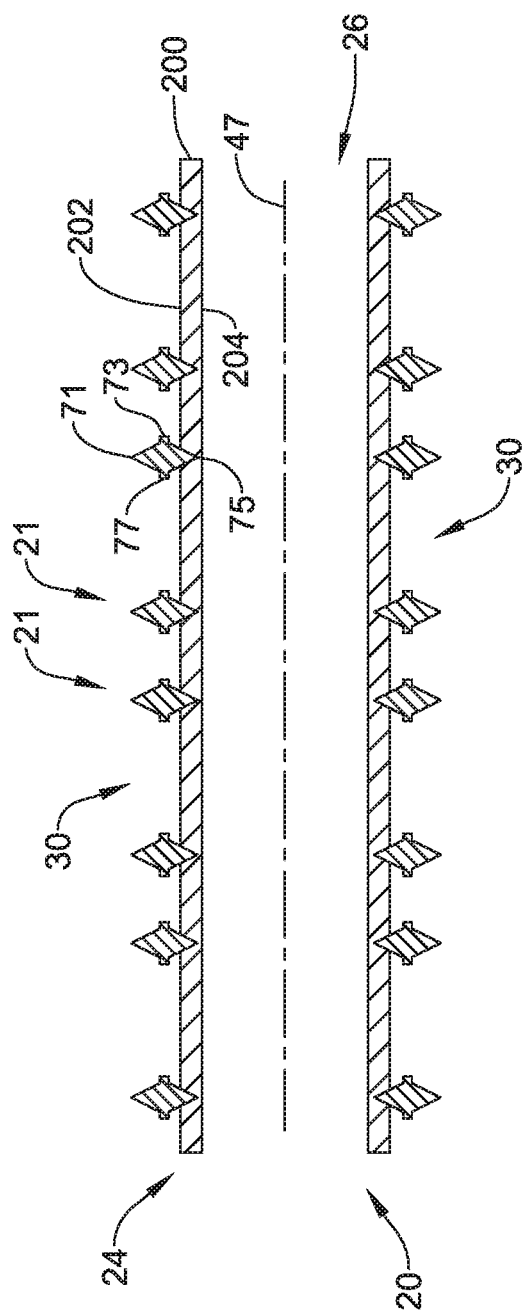

In the embodiment of FIG. 21, the covering layer 200 may cover the framework such that the one or more wires 21 may only be partially disposed around covering layer 200. For instance, first tapered points 71 may be disposed radially further away from central longitudinal axis 47 than outer wall surface 202 of covering layer 200. However, outer wall surface 202 of covering layer 200 may be disposed radially further away from central longitudinal axis 47 than second tapered points 75. In some embodiments, second tapered points 75 may still be disposed radially further away from central longitudinal axis 47 than inner wall surface 204 of covering layer 200. In such embodiments, second tapered points 75 may be embedded within covering layer 200. Although FIG. 21 depicts both first and second projections 73, 77 disposed radially further away from central longitudinal axis 47 than outer wall surface 202 of covering layer 200, in other embodiments one or more of first and second projections 73, 77 may be embedded within covering layer 200. In these embodiments, covering layer 200 may be disposed at least partially in open cells 30 between the one or more wires 21. Additionally, although FIG. 21 depicts first and second tapered points 71, 75 as extending generally perpendicular to central longitudinal axis 47, in other embodiments, the one or more wires 21 may be disposed rotated with respect to central longitudinal axis 47 such that first and second tapered points 71, 75 extend at any angle with respect to central longitudinal axis 47.

Figure 22:
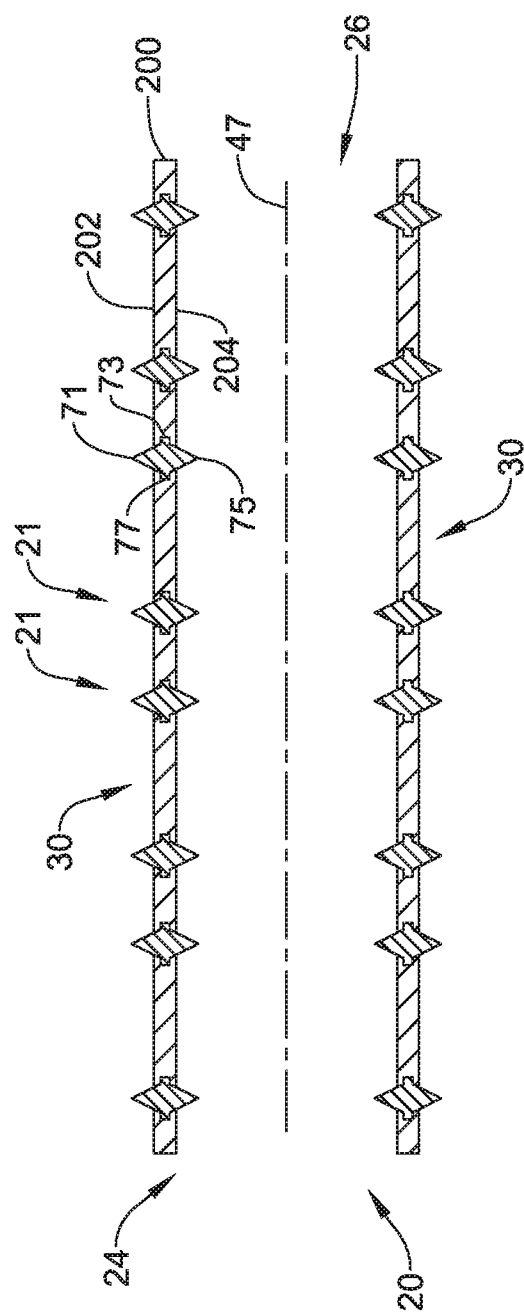

In the embodiment of FIG. 22, the covering layer 200 may cover the framework such that at least a portion of the one or more wires 21 may be disposed radially closer to central longitudinal axis 47 than inner wall surface 204 of covering layer 200 while at least a portion of the one or more wires 21 may be disposed radially further away from central longitudinal axis 47 than outer wall surface 202 of covering layer 200. For instance, first tapered points 71 may be disposed radially further away from central longitudinal axis 47 than outer wall surface 202 of covering layer 200, while second tapered points 75 may be disposed radially closer to central longitudinal axis 47 than inner wall surface 204 of covering layer 200. In these embodiments, covering layer 200 may be disposed in open cells 30 between the one or more wires 21. Further, although depicted in FIG. 22 with both first and second projections 73, 77 embedded within covering layer 200, in other embodiments only one of first and second projections 73, 77 may be embedded with the other of first and second projections 73, 77 disposed either radially closer to central longitudinal axis 47 than inner wall surface 204 of covering layer 200 or radially further away from central longitudinal axis 47 than outer wall surface 202 of covering layer 200. Additionally, although FIG. 22 depicts first and second tapered points 71, 75 as extending generally perpendicular to central longitudinal axis 47, in other embodiments, the one or more wires 21 may be disposed rotated with respect to central longitudinal axis 47 such that first and second tapered points 71, 75 extend at any angle with respect to central longitudinal axis 47.

Figure 23:
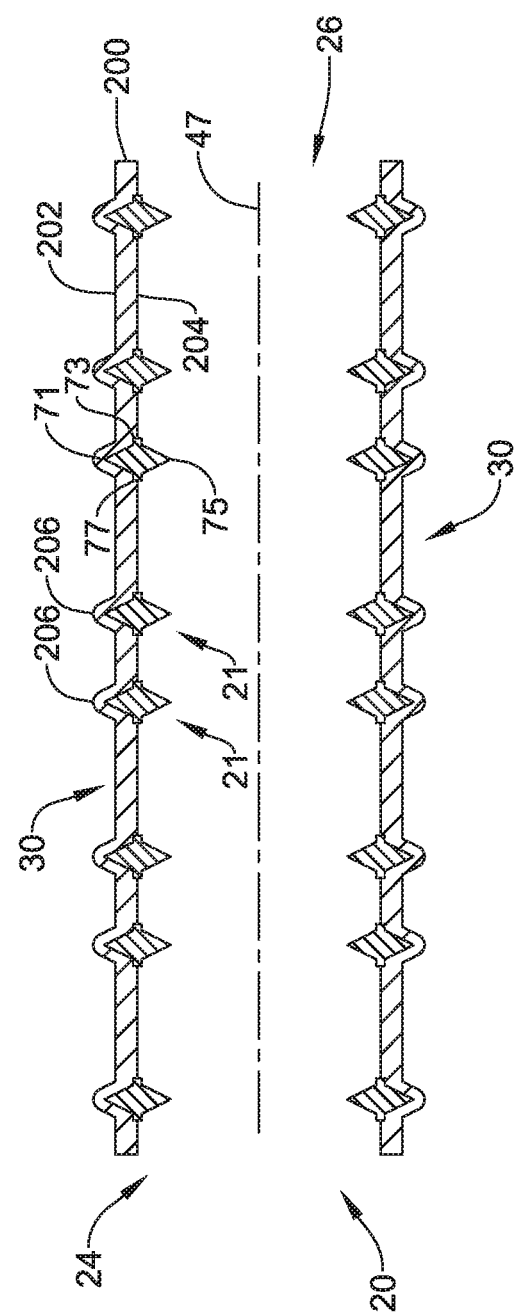

In the embodiment of FIG. 23, the covering layer 200 may cover the framework such that covering layer 200 may disposed at least partially around the one or more wires 21. For instance, outer wall surface 202 of covering layer 200 may be disposed radially further away from central longitudinal axis 47 than first tapered points 71 where first tapered points 71 contact covering layer 200. However, in at least some of these embodiments, first tapered points 71 may be disposed radially further away from central longitudinal axis 47 than inner wall surface 204 of covering layer 200. In these embodiments, first tapered points 71 may be embedded within covering layer 200. Further, in various different embodiments, first and second projections 73, 77 may be embedded within covering layer 200, may be disposed radially closer to central longitudinal axis 47 than inner wall surface 204 of covering layer 200, or may be disposed radially further away from central longitudinal axis 47 than outer wall surface 202 of covering layer 200. In at least some embodiments, first and second projections 73, 77 may disposed in different locations with respect to each other. In these embodiments, covering layer 200 may be disposed at least partially in open cells 30 between the one or more wires 21. In some of these embodiments, outer wall surface 202 of covering layer 200 may include bumps 206 where first tapered points 71 is embedded within covering layer 200 (and may include additional bumps 206 in embodiments where other tapered points are embedded within covering layer 200). Additionally, although FIG. 23 depicts first and second tapered points 71, 75 as extending generally perpendicular to central longitudinal axis 47, in other embodiments, the one or more wires 21 may be disposed rotated with respect to central longitudinal axis 47 such that first and second tapered points 71, 75 extend at any angle with respect to central longitudinal axis 47.

Figure 24:
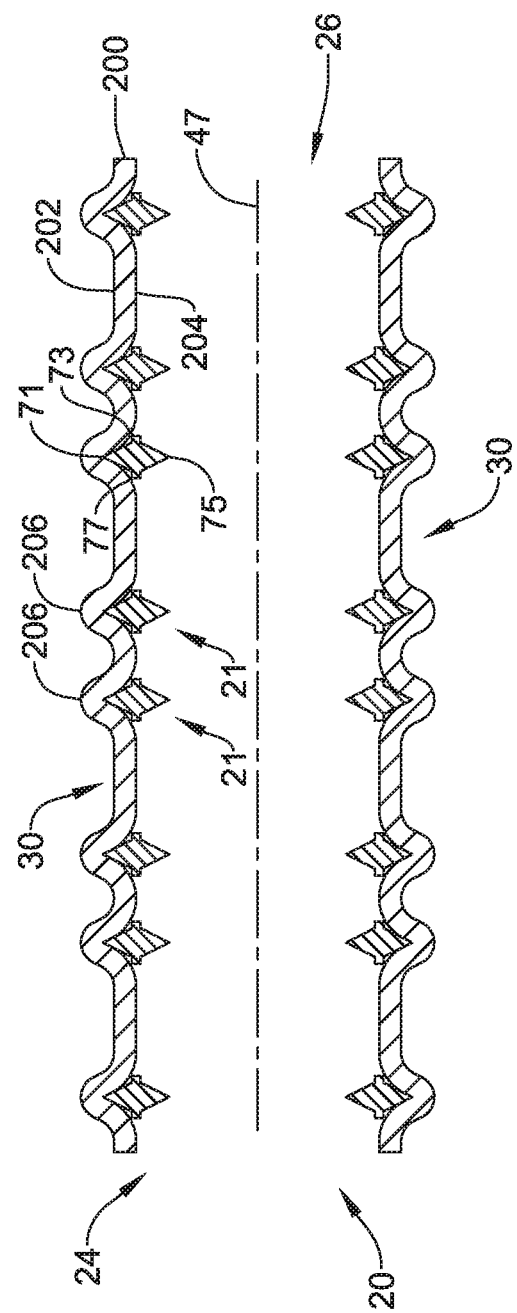

In the embodiment of FIG. 24, the covering layer 200 may cover the framework such that the entirety of covering layer 200 may disposed completely over the one or more wires 21. For instance, both outer wall surface 202 and inner wall surface 204 of covering layer 200 may be disposed radially further away from central longitudinal axis 47 than all of the one or more wires 21, including first tapered points 71, where the one or more wires contacts covering layer 200 at any cross-section perpendicular to the longitudinal axis 47. In these embodiments, covering layer 200 may be disposed at least partially in open cells 30 between the one or more wires 21. In some of these embodiments, outer wall surface 202 of covering layer 200 may include bumps 206 proximate first tapered points 71. Additionally, although FIG. 24 depicts first and second tapered points 71, 75 as extending generally perpendicular to central longitudinal axis 47, in other embodiments, the one or more wires 21 may be disposed rotated with respect to central longitudinal axis 47 such that first and second tapered points 71, 75 extend at any angle with respect to central longitudinal axis 47.

Figure 25:
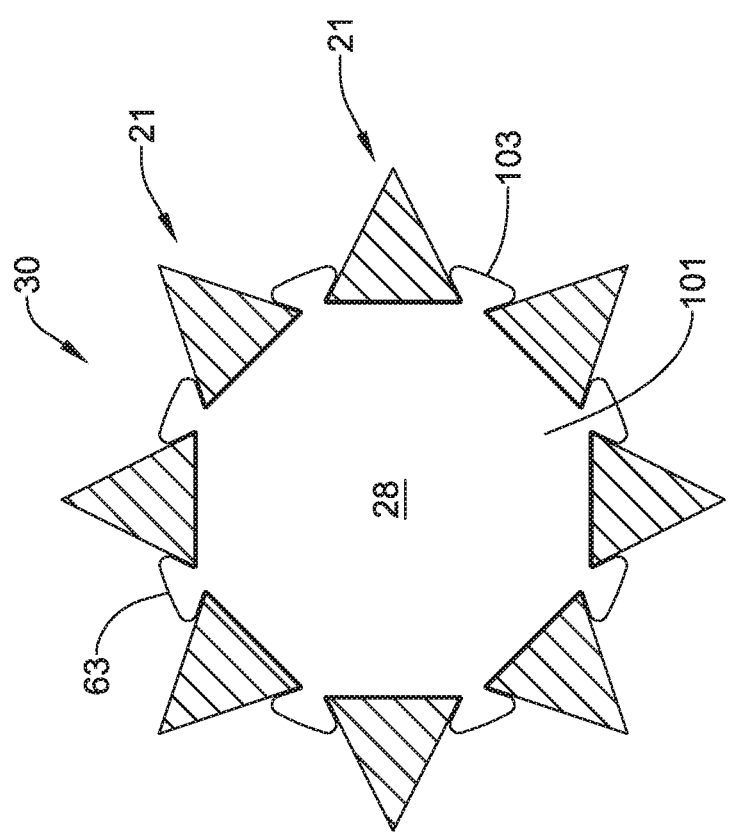
FIG. 25 is an example cross-section of an endoprosthesis including a covering layer during forming of the endoprosthesis, in accordance with embodiments of the present disclosure.
Figure 26:
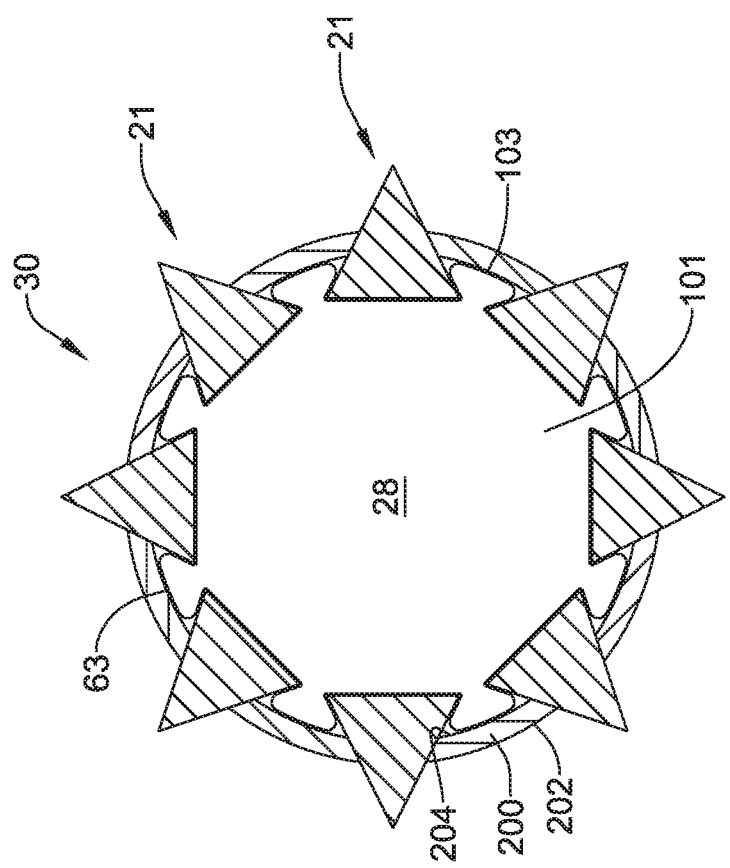
FIG. 26 is another example cross-section of an endoprosthesis including a covering layer during forming of the endoprosthesis, in accordance with embodiments of the present disclosure.
Figure 27:
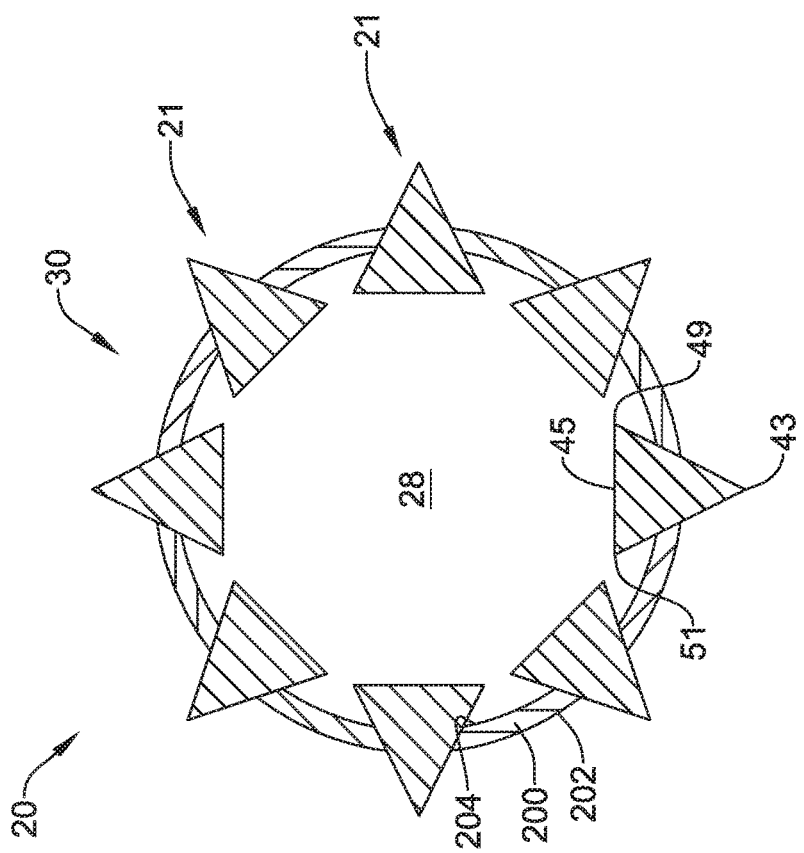
FIG. 27 is an example cross-section of an endoprosthesis including a covering layer after forming of the endoprosthesis, in accordance with embodiments of the present disclosure.

FIGS. 25-27 depict example cross-sections of endoprosthesis 20 in accordance with the present disclosure at various stages of manufacture. In one example method, the one or more wires 21 are woven to create woven wire framework 22, including open cells 30. Next, a compliant filler 101 is inserted into lumen 28 of woven wire framework 22. FIG. 25 depicts a cross-section of endoprosthesis 20 at this stage. Compliant filler 101 may be a compliant solid rod or a compliant hollow tube, a compressible foam, or a curable material, for example. In some instances, the compliant filler 101 may be made out of a polymer material. In some embodiments, compliant filler 101 may have an outer diameter that is greater than the inner diameter of woven wire framework 22 as measured from one wire 21 to another wire 21 across lumen 28. In such embodiments, due to the compliant nature of compliant filler 101, portions 103 of compliant filler 101 may extend radially out into open cells 30 between the one or more wires 21. In some embodiments, a portion of wires 21, such as tapered points, may extend radially outward beyond the outer extent of the compliant filler 101.

Once compliant filler 101 is in place, a liquid material, such as a polymeric material, may be applied to the wire framework 22, such as during a spray coating or dip coating process, resulting in liquid material flowing into open cells 30. Once the liquid material is in place, the liquid material may be cured or hardened into a solid material, such as by application of heat, electricity, ultraviolet light, or a cross-linking agent, for example. After curing or hardening, the liquid material may form covering layer 200. FIG. 26 depicts a cross-section of endoprosthesis 20 at this stage.

Thereafter, compliant filler 101 may be removed from endoprosthesis 20. FIG. 27 depicts an example cross-section of endoprosthesis 20 with compliant filler 101 removed, leaving covering material spanning cells 30 between adjacent wires 22. In this way, an endoprosthesis 20 similar to those described with respect to FIGS. 12, 17, and 22 may be formed.

In additional or alternative embodiments, a liquid material, such as a polymeric material, may be applied to the wire framework 22, such as during a spray coating or dip coating process. In these embodiments, after hardening of the liquid material, endoprosthesis 20 may have a structure similar to that described with respect to FIGS. 13, 14, 18, 19, and/or 23, 24.

In still additional or alternative embodiments, instead of using a liquid material, a solid cover material in the shape of a hollow tube or sheath may be positioned over the one or more wires 21 and may be disposed at least partially in open cells 30. Once the cover material is in place in open cells 30, the cover material forms covering layer 200 having an outer wall surface 202 and an inner wall surface 204. Some example cover materials include various polymers. In some embodiments, the cover material may be heat-shrunk or otherwise made to closely conform to the one or more wires 21.

FIGS. 28 and 29 depict example cross-sections of endoprosthesis 20 during another method of making an endoprosthesis 20 in accordance with the present disclosure. FIG. 28 depicts a cross-section of mandrel 111 covered by covering layer 200, such as a polymeric tubular member, having an outer wall surface 202 and an inner wall surface 204. Next, one or more wires 21 may be woven over mandrel 111 and covering layer 200 to form endoprosthesis 20, as depicted in FIGS. 29A and 29B in cross-section. FIG. 29A depicts the one or more wires 21 as triangles woven with faces 45 generally flat against to outer surface 202 of covering layer 200 with the one or more wires 21 disposed completely further away from the center of mandrel 111 than outer wall surface 202 of covering layer 200. FIG. 29B, in contrast, depicts an embodiment where wires 21 are generally diamond shaped and where at least a portion of the one or more wires 21 are be embedded within covering layer 200. That is, at least a portion of the one or more wires 21 are disposed closer to the center of mandrel 111 than outer wall surface 202 of covering layer 200. It should be understood that the specific shapes of wires 21 of FIGS. 29A and 29B are only exemplary, and in other embodiments, wires 21 having other shapes may be used. Additionally, in other embodiments, the one or more wires 21 may be rotated with respect to mandrel 111 and covering layer 200 such that one or more of tapered points 43, 49, and 51 may be pointed inward toward mandrel 111 and covering layer 200. In this way, an endoprosthesis 20 similar to those described with respect to FIGS. 10, 11, 15, 16, and/or 20, 21 may be formed.

Figure 30:
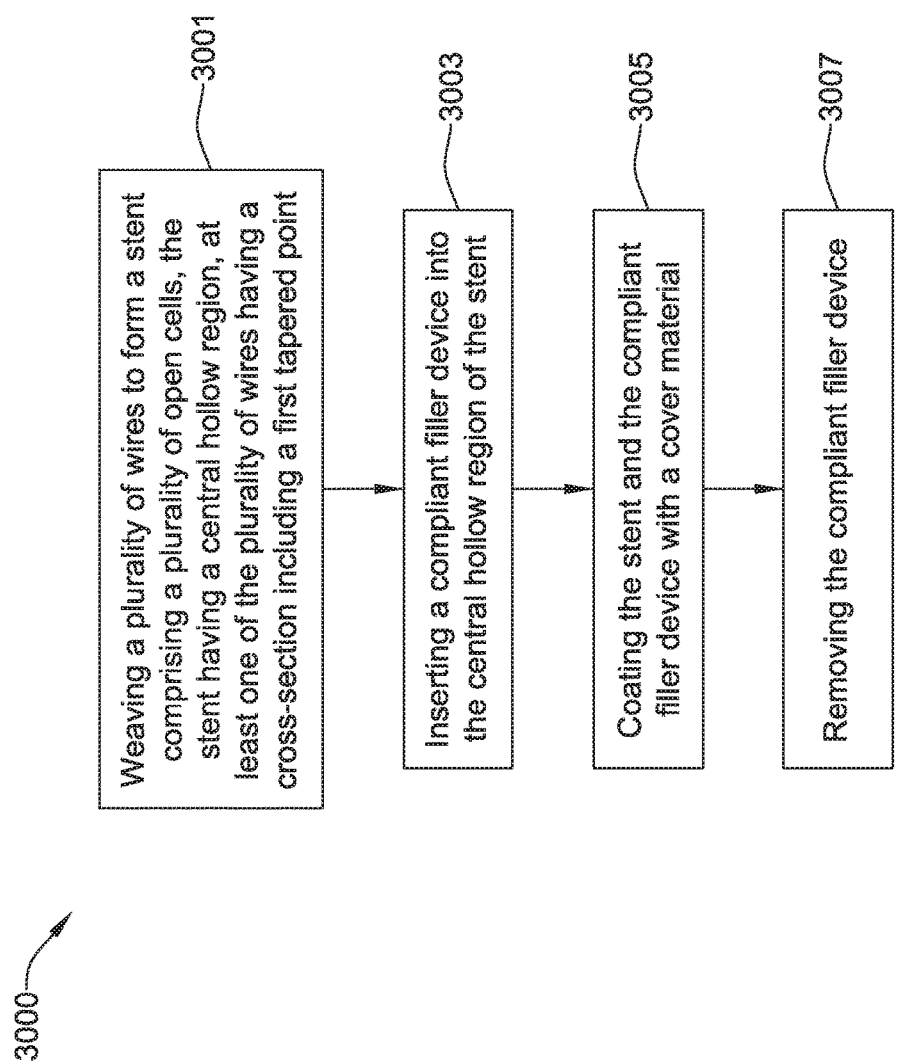
FIG. 30 is a flow diagram of a method of forming an endoprosthesis, in accordance with the present disclosure.

FIG. 30 is a flow diagram illustrating a method that may be used to form an endoprosthesis 20 in accordance with the present disclosure, for example those described with respect to FIGS. 10-24. The method may begin by weaving, such as braiding, a plurality of wires to form a stent comprising a plurality of open cells, the stent having a central hollow region, at least one of the plurality of wires having a cross-section including a first tapered point, as at 3001. The method may further include inserting a compliant filler into the central hollow region of the stent, as at 3003. The method may then include covering, e.g., coating, the stent and the compliant filler with a cover material, as at 3005. Finally, the method may include removing the compliant filler device, as at 3007.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. An implantable medical device for implantation within a passageway of a patient, the device comprising:
   a tubular framework including a plurality of interwoven wires, at least one of the plurality of interwoven wires comprising a cross-section having a first tapered point, the cross-section of the at least one wire taken transverse to a longitudinal length of the wire such that the first tapered point extends along the longitudinal length of the wire;
   a covering layer having a central longitudinal axis and an inner diameter and an outer diameter;
   wherein the covering layer covers at least a portion of the framework and extends between adjacent wires of the plurality of interwoven wires included in the portion of the framework, and
   wherein the first tapered point extends outward further than the outer diameter of portions of the covering layer that extend between the adjacent wires.

2. The implantable medical device of claim 1, wherein the at least one of the plurality of interwoven wires has a cross-section having a second tapered point.

3. The implantable medical device of claim 2, wherein the second tapered point extends inward further than the outer diameter of the portions of the covering layer that extend between the adjacent wires.

4. The implantable medical device of claim 2, wherein the second tapered point extends inward further than the inner diameter of the portions of the covering layer that extend between the adjacent wires.

5. The implantable medical device of claim 2, wherein the cross-section of the at least one of the plurality of interwoven wires further comprises a third tapered point.

6. The implantable medical device of claim 2, wherein the first tapered point extends outward in a direction opposite the second tapered point.

7. The implantable medical device of claim 1, wherein the cross-section of the at least one of the plurality of interwoven wires is triangular.

8. The implantable medical device of claim 1, wherein the cross-section of the at least one of the plurality of interwoven wires further comprises a rectangular projection.

9. An implantable medical device for implantation within a passageway of a patient, the device comprising:
   a tubular framework including a plurality of interwoven wires, at least one of the plurality of interwoven wires comprising a cross-section having a first tapered point oriented radially outward from a central longitudinal axis of the framework, the cross-section of the at least one wire taken transverse to a longitudinal length of the wire such that the first tapered point extends along the longitudinal length of the wire; and
   a covering layer disposed over the framework and extending between adjacent wires of the plurality of interwoven wires, the covering layer having an inner diameter and an outer diameter;
   wherein the first tapered point is embedded in the covering layer and forms a radially outward extending bump in an outer wall surface of the covering layer extending radially outward of the outer diameter of the covering layer.

10. The implantable medical device of claim 9, wherein the at least one of the plurality of interwoven wires has a cross-section having a second tapered point.

11. The implantable medical device of claim 10, wherein the second tapered point extends inward further than the outer diameter of portions of the covering layer that extend between the adjacent wires.

12. The implantable medical device of claim 10, wherein the second tapered point extends inward further than the inner diameter of portions of the covering layer that extend between the adjacent wires.

13. The implantable medical device of claim 10, wherein the cross-section of the at least one of the plurality of interwoven wires further comprises a third tapered point.

14. The implantable medical device of claim 9, wherein the cross-section of the at least one of the plurality of interwoven wires is triangular.

15. The implantable medical device of claim 9, wherein an inner diameter of the framework is radially inward of the inner diameter of the covering layer.

16. The implantable medical device of claim 9, wherein the at least one of the plurality of interwoven wires includes a face parallel to the central longitudinal axis.

17. The implantable medical device of claim 16, wherein the face is radially inward of the inner diameter of portions of the covering layer that extend between the adjacent wires.

18. An implantable medical device for implantation within a passageway of a patient, the device comprising:
   a tubular framework including a plurality of interwoven wires, at least one of the plurality of interwoven wires comprising a cross-section having a first tapered point oriented radially outward from a central longitudinal axis of the framework, the cross-section of the at least one wire taken transverse to a longitudinal length of the wire such that the first tapered point extends along the longitudinal length of the wire; and
   a covering layer disposed over a portion of the framework and extending between adjacent wires of the plurality of interwoven wires included in the portion of the framework;
   wherein the first tapered point extends radially outward further than an outer diameter of portions of the covering layer that extend between the adjacent wires, and
   wherein the first tapered point is embedded in the covering layer and forms a radially outward extending bump in an outer wall surface of the covering layer that extends radially outward further than the first tapered point.

19. The implantable medical device of claim 18, wherein the cross-section of the at least one of the plurality of interwoven wires has a second tapered point.

20. The implantable medical device of claim 18, wherein the cross-section of the at least one of the plurality of interwoven wires is triangular.

* * * * *